United States Patent
Sakakibara

(10) Patent No.: US 7,872,782 B2
(45) Date of Patent: Jan. 18, 2011

(54) OPTICAL SCANNER AND METHOD OF CONTROLLING OPTICAL SCANNER

(75) Inventor: Masahiro Sakakibara, Nagoya (JP)

(73) Assignee: Brother Kogyo Kabushiki Kaisha, Nagoya (JP)

( * ) Notice: Subject to any disclaimer, the term of this patent is extended or adjusted under 35 U.S.C. 154(b) by 788 days.

(21) Appl. No.: 11/902,444

(22) Filed: Sep. 21, 2007

(65) Prior Publication Data

US 2008/0043295 A1    Feb. 21, 2008

Related U.S. Application Data

(63) Continuation-in-part of application No. PCT/JP2006/306687, filed on Mar. 30, 2006.

(30) Foreign Application Priority Data

Mar. 30, 2005    (JP)    ............................. 2005-097671

(51) Int. Cl.
     *H04N 1/04*    (2006.01)
(52) U.S. Cl. .................. 358/481; 358/511; 358/474
(58) Field of Classification Search ................ 358/481, 358/511, 474; 359/223, 224
See application file for complete search history.

(56) References Cited

U.S. PATENT DOCUMENTS 7,446,911 B2 * 11/2008 Asai et al. .................... 358/481
7,639,413 B2 * 12/2009 Nishikawa et al. ......... 359/224.1
2005/0219674 A1   10/2005   Asai et al.

FOREIGN PATENT DOCUMENTS

| EP | 1 586 933 A1 | 10/2005 |
|---|---|---|
| JP | A 01-302316 | 12/1989 |
| JP | A 09-101474 | 4/1997 |
| JP | A 09-230279 | 9/1997 |
| JP | A 2001-021829 | 1/2001 |
| JP | A 2004-191953 | 7/2004 |
| WO | WO 2004-049035 A1 | 6/2004 |

* cited by examiner

*Primary Examiner*—Houshang Safaipour
(74) *Attorney, Agent, or Firm*—Oliff & Berridge PLC

(57) ABSTRACT

An optical scanner has an oscillation-type optical scanning mechanism which includes a movable member which resonates at a predetermined resonance frequency, a drive signal generator which generates a drive signal for allowing the movable member to resonate at the resonance frequency, and an oscillation signal generator which generates an oscillation signal in response to a change of the radiation direction of the light beams. Here, the oscillation signal generator includes a dot clock generator which generates a dot clock which becomes the reference of time-series processing by setting a frequency of the oscillation signal as a reference frequency.

9 Claims, 10 Drawing Sheets

OPTICAL SCANNER AND METHOD OF CONTROLLING OPTICAL SCANNER

BACKGROUND OF THE INVENTION

The present invention relates to an optical scanner and a method of controlling the optical scanner, and more particularly to an optical scanner which scans light beams by oscillating a movable member at intrinsic resonance frequency thereof and a control method of the optical scanner.

An optical scanner which is represented by a laser beam printer or a projector which projects an image by scanning light beams has been conventionally used in various industrial fields. Such an optical scanner adopts an optical scanning mechanism which changes the direction of light and, recently, as a type of the mechanism, an oscillation-type optical scanning mechanism has been attracting attentions from a viewpoint of miniaturization of the device.

In one conventional example of the oscillation-type optical scanning mechanism, light beams are scanned such that an oscillating body having a reflecting mirror portion is oscillated so as to change the reflection direction of light beams incident on the reflecting mirror portion.

The oscillating body is configured to include the reflecting mirror portion, a fixed frame portion, a resilient deformation portion made of a resilient material or the like which is connected to the reflecting mirror portion and the fixed frame portion, and a drive source which imparts the deformation to the resilient deformation portion. Here, as the drive source, a drive source which makes use of an electrostatic force, an electromagnetic force, an action of heat, a piezoelectric action or the like can be named.

Further, in many conventional optical scanners, all operations of the optical scanner including the optical scanning mechanism is managed and controlled based on a master clock which constitutes a basis of time-series processing. However, a frequency of this master clock is fixed. That is, image data is read from an external device based on the master clock, and light beams are scanned based on the master clock and hence, it is possible to acquire a proper amount of image data from the outside and, at the same time, the light beams can be scanned as a visible light spot at a spatial position where an image is expected by changing the radiation direction of the light beams.

Patent document 1 discloses in detail the optical scanner which uses the oscillation-type optical scanning mechanism for scanning light beams in the horizontal direction. The summary of the invention disclosed in patent document 1 is explained hereinafter in conjunction with FIG. 11.

An optical scanner 100 shown in FIG. 11 is configured to directly project an image on a retina of a viewer. The optical scanner 1 includes a light source unit part 101, a vertical scanning system 102, a horizontal scanning system 103 and relay optical systems 126, 127.

In the scanning optical system 103, an oscillation-type optical scanning mechanism 104 which is constituted by combining a piezoelectric element and an oscillating reflecting mirror is driven in response to a drive signal from a horizontal scanning drive circuit 121. When light beams are radiated to the reflecting mirror, scanned light beams are received by a beam detector (BD) 123 which detects a RD signal. Then, in a signal processing circuit 105 provided to a light source unit part 101, a horizontal synchronizing signal based on a master clock and the BD signal is generated. Further, in the horizontal scanning drive circuit 121, the above-mentioned drive signal is obtained using the horizontal synchronizing signal as the reference.

Here, it is considered desirable to set frequency for driving the oscillation-type optical scanning mechanism 104 (scanning frequency in the horizontal direction) to a value substantially equal to resonance frequency of a-movable member of the oscillation-type optical scanning mechanism 104 for stabilizing an oscillating state. Further, in a field of control technique, a technique which oscillates a movable member of an actuator at a resonance frequency for acquiring a large variable range in a miniaturized actuator is known (for example, see patent document 1). Patent document 1: JP-A-2004-191953

SUMMARY OF THE INVENTION

However, a Q (quality factor) of a resonance system of the oscillation-type optical scanning mechanism usually covers several hundreds kinds and hence, when the horizontal scanning frequency deviates slightly from the resonance frequency, an operation of the resonance system is drastically changed. On the other hand, the resonance frequency of the oscillation-type optical scanning mechanism is changed in response to temperature, moisture or the like and, at the same time, there also exists individual difference for every oscillation-type optical scanning mechanism.

Accordingly, when scanning of light beams is performed using the oscillation-type optical scanning mechanism which is driven in response to a drive signal based on the master clock and the BD signal explained in the Background Art, the resonance frequency of the movable member of the oscillation-type optical scanning mechanism and the scanning frequency given from the outside differ from each other and hence, there arises a case in which a sufficient scanning range is not acquired or stable horizontal scanning cannot be performed as a result of a fact that the distribution of a change width of the scanning range extends over a wide range thus giving rise to a possibility that the performance of the optical scanner is lowered.

To overcome such a task, the present invention provides an optical scanner which includes a light beam generating part which generates light beams in response to an image signal, an optical path part which guides the light beams to a projection screen, and an optical scanning part which changes the radiation direction of the light beams, wherein the optical scanning part includes an oscillation-type optical scanning mechanism which includes a movable member which resonates at a predetermined resonance frequency for changing the radiation direction of the light beams, a drive signal generator which generates a drive signal for allowing the movable member to resonate at the resonance frequency, and an oscillation signal generator which generates an oscillation signal in response to a change of the radiation direction of the light beams, and the light beam generating part includes a dot clock generator which generates a dot clock which becomes the reference of time-series processing by setting a frequency of the oscillation signal as a reference frequency.

In this manner, the movable member of the oscillation-type optical scanning mechanism is oscillated at the resonance frequency and hence, even when the resonance frequency of the movable member of the oscillation-type optical scanning mechanism is changed due to an environment such as a temperature, a moisture or the like, or even when there exists difference in the resonance frequency attributed to the individual difference of the oscillation-type optical scanning mechanism, the optical scanner can perform stable optical scanning.

Further, by providing the oscillation-type optical scanning mechanism with a reflecting mirror which is fixed to the movable member and reflects the light beams, a first resilient member which is connected to the reflecting mirror and generates torsional oscillations, and a driving piezoelectric element which biases the first resilient member, the radiation direction of the light beams can be changed using the reflecting mirror and hence, the attenuation of the light beams can be reduced thus oscillating the reflecting mirror at the resonance frequency whereby it is possible to acquire a large displacement of the light beams with small electric power.

Further, by providing the oscillation signal generator with a second resilient member which is connected to the reflecting mirror and transmits the torsional oscillations and a detecting piezoelectric element which generates the oscillation signal in response to a torsional quantity of the second resilient member, it is possible to integrally form the oscillation signal generator and the oscillation-type optical scanning mechanism.

Further, by allowing the oscillation signal generator to produce the oscillation signal from the drive signal, it is possible to obtain the oscillation signal from the drive signal and hence, it is unnecessary to provide a sensor such as a beam detector.

Further, by allowing the drive signal generator to generate the oscillation using the oscillation signal as the drive signal by a positive feedback, the positive-feedback oscillation can be performed with the positive feedback and hence, the movable member is always held in a resonance state whereby a large displacement of light beams can be obtained.

Further, by allowing the drive signal generator to generate the drive signal which restricts the radiation direction of the light beam within a predetermined range, it is possible to set a scanning range of light spot within a predetermined range thus controlling a size of an image generated by the light spot.

Further, by providing the optical path part with an optical element which corrects the passing direction of the light beams using an arc sine function, it is possible to enhance image quality of an image generated by a light spot.

Further, by providing the dot clock generator with a phase-locked loop and by multiplying the frequency of the oscillation signal so as to generate a dot clock which becomes the reference of time-series processing, even when the frequency of the oscillation signal is changed in a wide range, it is possible to accurately multiply the frequency.

Further, the present invention provides a control method of an optical scanner which scans a light spot on a projection screen by changing the radiation direction of light beams whose intensity is modulated based on a dot clock using an optical element, wherein a position of the light spot on the projection screen is oscillated at a resonance frequency intrinsic to the optical element, an oscillation signal is generated in response to a change of the radiation direction of the light beams, and the dot clock is generated using the frequency of the oscillation signal as the reference frequency.

In this manner, by adopting the control method of an optical scanner which oscillates the position of the light spot on the projection screen at the resonance frequency thus forming the oscillation signal, and generates the clock using the frequency of the oscillation signal as the reference frequency, even when the resonance frequency intrinsic to the optical element is changed due to an environment such as a temperature or a moisture, or even when there exists difference in resonance frequency attributed to the individual reference, the optical scanner can perform stable optical scanning.

According to the present invention, the movable member of the oscillation-type optical scanning mechanism is oscillated at the resonance frequency and hence, even when the resonance frequency of the movable member of the oscillation-type optical scanning member is changed due to the environment such as the temperature or the moisture, or even when there exists the difference in resonance frequency attributed to the individual difference of the oscillation-type optical scanning mechanism, the optical scanner can perform stable optical scanning.

BRIEF EXPLANATION OP THE DRAWINGS

DESCRIPTION OF THE PREFERRED EMBODIMENTS

Figure 1:
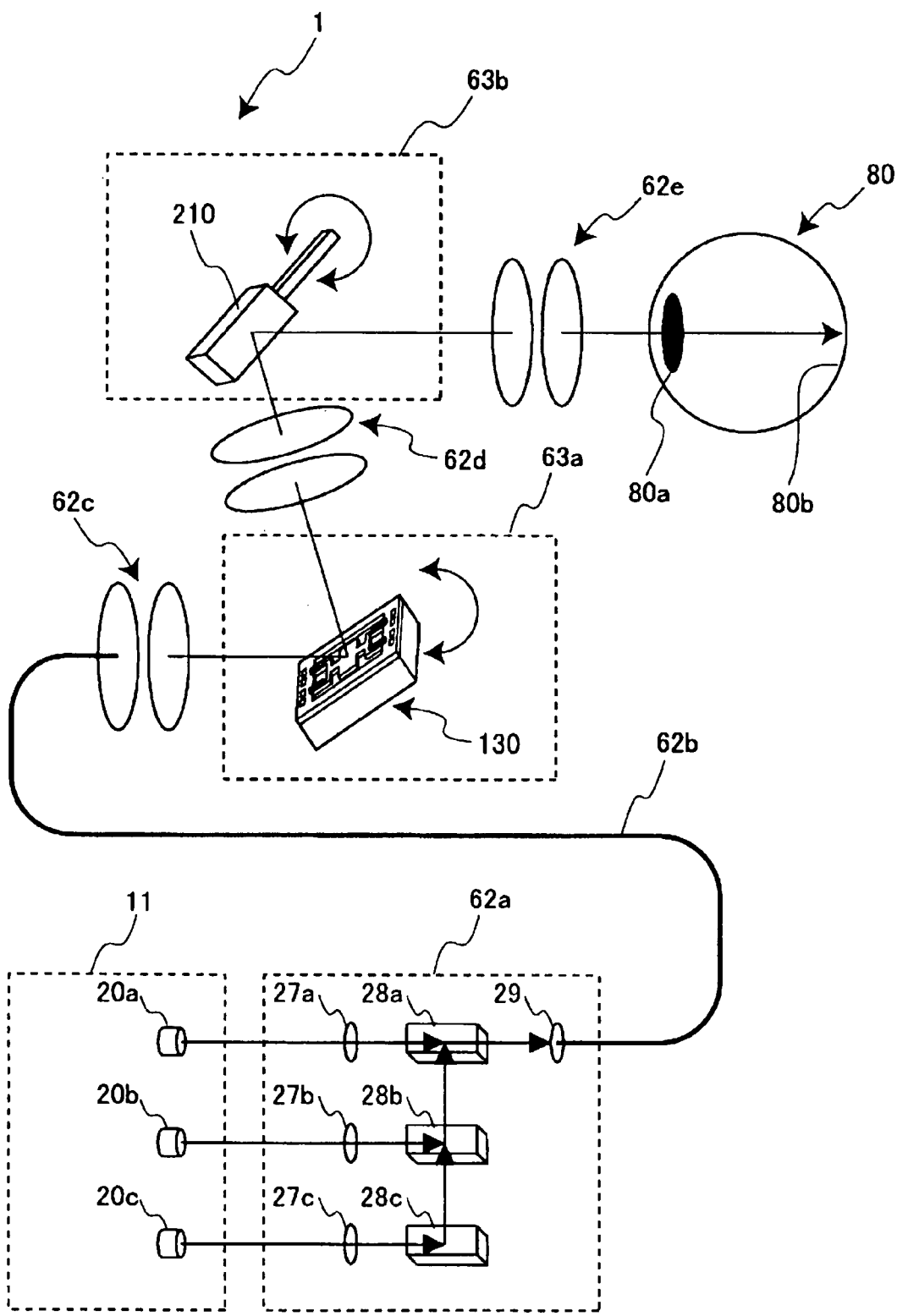
FIG. 1 is a conceptual view of an optical scanner according to an embodiment.

An optical scanner according to this embodiment which includes a light beam generating part which generates light beams in response to an image signal, an optical path part which guides the light beams to a projection screen, and an optical scanning part which changes the radiation direction of the light beams, wherein the optical scanning part includes an oscillation-type optical scanning mechanism which includes a movable member which resonates at a predetermined resonance frequency for changing the radiation direction of the light beams, a drive signal generator which generates a drive signal for allowing the oscillation-type optical scanning mechanism to resonate at the resonance frequency, and an oscillation signal generator which generates an oscillation signal in response to a change of the radiation direction of the light beams, and the light beam generating part includes a dot clock generator which generates a dot clock which becomes the reference of time-series processing by setting a frequency of the oscillation signal as a reference frequency.

Here, the oscillation-type optical scanning mechanism is not particularly limited provided that the oscillation-type optical scanning mechanism is a mechanism for imparting a change to the radiating direction of the light beams. However, it is important in this embodiment that the mechanism constitutes the resonance system. As an example, the radiating direction of the light beams may be changed by reflecting the light beams on an oscillating reflecting mirror (a mirror surface).

Then, the reflecting mirror is biased by the driving force and is oscillated at an intrinsic frequency which a resonance system possesses. Although the biasing of the reflecting mirror may be based on various driving forces such as a piezoelectric force, an electromagnetic force, an electrostatic force, a thermal deformation force and the like, the use of the piezoelectric force particularly contributes to the miniaturization of the device.

That is, when the piezoelectric element is used for biasing the reflecting mirror, by providing the oscillation-type optical scanning mechanism which includes a reflecting mirror which reflects the light beams, a first resilient member which is connected to the reflecting mirror and generates torsional oscillations for oscillating a movable member at a resonance frequency, and a driving piezoelectric element which biases the first resilient member, it is possible to achieve the miniaturization, the reduction of weight and the lowering of cost of the oscillation-type optical scanning mechanism and also the optical scanner.

Further, the oscillation signal generator which generates the oscillation signal in response to a change of the radiation direction of the light beams is not particularly limited provided that the oscillation signal generator eventually generates an electric signal as a result of a piezoelectric action, an electromagnetic action, an electrostatic action or the like. However, the use of the piezoelectric action particularly contributes to the miniaturization of the device.

That is, as one constitution of the oscillation signal generator which uses the piezoelectric element, the oscillation signal generator may include a second resilient member which is connected to the reflecting mirror and transmits the torsional oscillations of resonance frequency, and a detecting piezoelectric element which detects a strain of the second resilient member. Due to such a constitution, by way of the first resilient member which is connected to the reflecting mirror and constitutes the oscillation-type optical scanning mechanism and the second resilient member which is connected to the reflecting mirror and constitutes the oscillation signal generator, it is possible to easily form the oscillation-type optical scanning mechanism and the oscillation signal generator into an integral body and hence, the miniaturization, the reduction of weight and the lowering of cost of the optical scanner can be realized.

Further, the oscillation signal generator may be integrally formed with the oscillation-type optical scanning mechanism to generate self-excited oscillations by itself. By performing a positive-feedback oscillation of the oscillation signal, it is possible to oscillate the movable member at a resonance frequency.

Further, to generate the positive-feedback oscillation of the oscillation signal, for example, the drive signal generator may generate the positive-feedback oscillation by changing a phase transition quantity of the oscillation signal using a phase shift circuit. That is, the oscillation-type optical scanning mechanism exhibits properties of a two or more higher-order system in the vicinity of the resonance frequency and hence, again property of the oscillation-type optical scanning system is sharply elevated at the resonance frequency and a phase property is largely changed (for example, approximately 180°) around the resonance frequency. Accordingly, by providing a phase shifter having a proper phase property to a feedback control system, it is possible to accurately generate the self-excited oscillation at the resonance frequency. In such self-excited oscillation, even when the resonance frequency of the movable member of the oscillation-type optical scanning mechanism is changed corresponding to a temperature and differs due to individual differences, it is possible to oscillate the movable member at the resonance frequency.

Further, the drive signal generator may set the radiation direction of light beams within a predetermined range. For example, by providing an AGC circuit, it is possible to scan the light beams within a predetermined range irrespective of the temperature property or the individual difference of the oscillation-type optical scanning mechanism.

The optical path part may include an optical element which corrects the passing direction of the light beams using an arc sine function. When the movable member for changing the radiation direction of the light beams is oscillated at the resonance frequency, image information for every dot clock which assumes the non-uniform distribution expressed by a sine function can obtain the uniform information density in the scanning direction using an optical element which corrects the passing direction of the light beams with an inverse sine function and hence, an image quality can be enhanced.

That is, the light beam generating part of this embodiment includes a dot clock generator, and a generated dot clock is used as a reference of time-series processing in the optical scanner. On the other hand, when the light beams are radiated to the movable member which resonates at the resonance frequency and signal processing is performed using the dot clock having an approximately uniform cycle as the reference, in spite of a fact that a motion of the movable member exhibits a sinusoidal wave, the dot clock substantially maintains uniformity with time (cycle being approximately fixed) and hence, when image data sampled based on an external clock is processed with the dot clock, an image generated by scanning a light spot produces a spatial strain.

Here, the dot clock is a clock which uses time from one dot which is a minimum unit of a displayed light spot to another dot as a unit. This dot clock is a signal having a frequency integer times as large as the resonance frequency which the movable member of the oscillation-type optical scanning mechanism possesses. On the other hand, the external clock is a clock which uses time from one dot which is a minimum unit of an image when the image is fed to the light beam generating part from an external device such as a host computer, a broadcasting facility or an optical disc drive device to another dot or time which is obtained by dividing the previous time by an integer as a unit time. This external clock is a signal having a fixed frequency which has X'tal (crystal oscillator) accuracy in the broadcasting facility and the optical disc drive device and does not depend on the individual differences of the device.

Here, the dot clock generator which generates the dot clock by multiplying the oscillation signal from the oscillation signal generator may include a phase-locked loop. When the clock is generated using the phase-locked loop, the clock having a wide high frequency range can be generated compared to a case which uses a VXO (variable Crystal oscillator), for example. Accordingly, the resonance frequency of the oscillation-type optical mechanism possesses a wide frequency range and hence, it is possible to easily multiply the frequency even when the frequency of the oscillation signal is changed in a wide range.

The control method of the optical scanner of this embodiment is a control method of an optical scanner which changes the radiation direction of light beams whose intensity is modulated based on the dot clock using an optical element, and scans a light spot on a projection screen, wherein positions of the light spot on the projection screen are oscillated at the resonance frequency intrinsic to the optical element thus generating an oscillation signal in response to the change of the radiation direction of the light beams, and the dot clock is generated by multiplying the frequency of the oscillation signal.

In generating the clock using such a method, the light spot is scanned on the projection screen using the optical element oscillated at the resonance frequency and, at the same time, the dot clock is generated by multiplying the frequency of the oscillation signal in response to the change of the radiation direction of the light beams and hence, it is possible to ensure the consistency with respect to the relationship between spatial positions of the light spots and a lapse of time of signal processing performed for every clock.

Hereinafter, several specific examples of the embodiment are explained in detail in conjunction with drawings.

FIG. 1 is a conceptual view of an optical scanner 1 according to the embodiment of the present invention. Hereinafter, the summary of the constitution and the manner of operation of the optical scanner 1 are explained.

The optical scanner 1 includes a light beam generating part 11, an optical path part and a light scanning part as main constitutional parts.

The optical path part is constituted of a light beam synthesizer 62a, an optical fiber 62b, a first lens unit 62c, a second lens unit 62d and a third lens unit 62e, and these parts are arranged in the optical scanner 1 in a dispersed manner.

The light scanning part is constituted of a horizontal scanning part 63a and a vertical scanning part 63b.

The optical scanner 1 acquires a video signal from an external device (not shown in the drawing), generates light beams of three colors of R (red), G (green) and B (blue) in response to the video signal, synthesizes the light beams using the light beam synthesizer 62a and, thereafter, guides the synthesized light beams to the vicinity of a human eyeball 80 using an optical fiber 62b thus forming an image of a light spot on a retina 80b using a third lens unit 62e and a crystalline lens 80a. Then, the horizontal scanning part 63a changes a direction of the light beams by scanning a light spot which is focused on the retina 80b in a horizontal direction, and the vertical scanning part 63b changes, a direction of the light beams by scanning the light-spot which is focused on the retina 80b of an image viewer in a vertical direction.

Such an optical scanner 1 scans the light spot two-dimensionally to allow an image viewer to recognize an image and is referred to as a retina-scanning-type display device.

Next, the respective parts of the optical scanner 1 are explained.

First of all, the optical path part is explained. The optical path part includes the light beam synthesizer 62a, the optical fiber 62b, the first lens unit 62c, the second lens unit 62d and the third lens unit 62e. The optical path part further includes a horizontal reflecting mirror 8 and a Galvano reflecting mirror 210. These members are arranged on the optical path to which the light beams are radiated in a state that the respective parts of the optical scanner 1 are arranged in a dispersed manner.

The light beams which are respectively emitted from a red laser light emitting element (hereinafter, abbreviated as "R laser") 20a, a green laser light emitting element (hereinafter, abbreviated as "G laser") 20b, and a blue laser light emitting element (hereinafter, abbreviated as "B laser") 20c which are arranged in the light beam generating part 11 are guided by these optical path parts and are finally focused by a crystalline lens 80a of the human eyeball 80, and an image of the light spot is formed on the retina 80b.

The light beam synthesizer 62a includes a collimating lens 27a, a collimating lens 27b, a collimating lens 27c, a dichroic reflecting mirror 28a, a dichroic reflecting mirror 28b, a dichroic reflecting mirror 28c, and a coupling lens 29. The light beams which are respectively emitted from the R laser 20a, the G laser 20b and the 1a laser 20c are formed into parallel lights using the collimating lens 27a, the collimating lens 27b, the collimating lens 27c and the parallel lights are synthesized using the dichroic reflecting mirror 28a, the dichroic reflecting mirror 28b, and the dichroic reflecting mirror 28c. The synthesized light beam is focused using a coupling lens 29 and is guided to the optical fiber 62b.

The optical fiber 62b guides the light beam to the horizontal scanning part 63a and the vertical scanning part 63b which are arranged in the vicinity of the eyeball 80.

The first lens unit 62c is provided for increasing a diameter of the light beam for reflecting the light beam which passes through the optical fiber 62b on the horizontal reflecting mirror 8.

The second lens unit 62d guides the light beam reflected by the horizontal reflecting mirror 8 to the Galvano reflecting mirror 210. The second lens unit may be formed of a correction optical element which converts a position of the light spot in a horizontal direction formed on the retina 80b using an inverse-sine function. By using such an optical element, it is possible to correct a strain of the two-dimensional image in the horizontal direction generated by the light spot even when the horizontal reflecting mirror 8 in the embodiment is oscillated in a sinusoidal wave state. The horizontal reflecting mirror 8 is fixed to the movable member so as to scan the light spot on the retina 80b in a horizontal direction.

The Galvano reflecting mirror 210 changes the reflection direction of the light beams so as to scan the light spot on the retina 80b in the vertical direction.

The third lens unit 62e is a lens unit for allowing the light beams which are reflected by the Galvano reflecting mirror 210 to pass through the crystalline lens 80a and forms the image of the light spot on the retina 80b.

Each one of the first lens unit 62c to the third lens unit 62e is constituted of a plurality of optical parts using a compound lens or the like so as to prevent the generation of aberration. To achieve the same objective, a single aspherical lens may be used as such a lens unit, and the constitution of the lens unit is not limited to the embodiment.

Next, the light beam generating part 11 which constitutes an essential part of the embodiment is explained in conjunction with views shown in FIG. 2 to FIG. 5.

Figure 2:
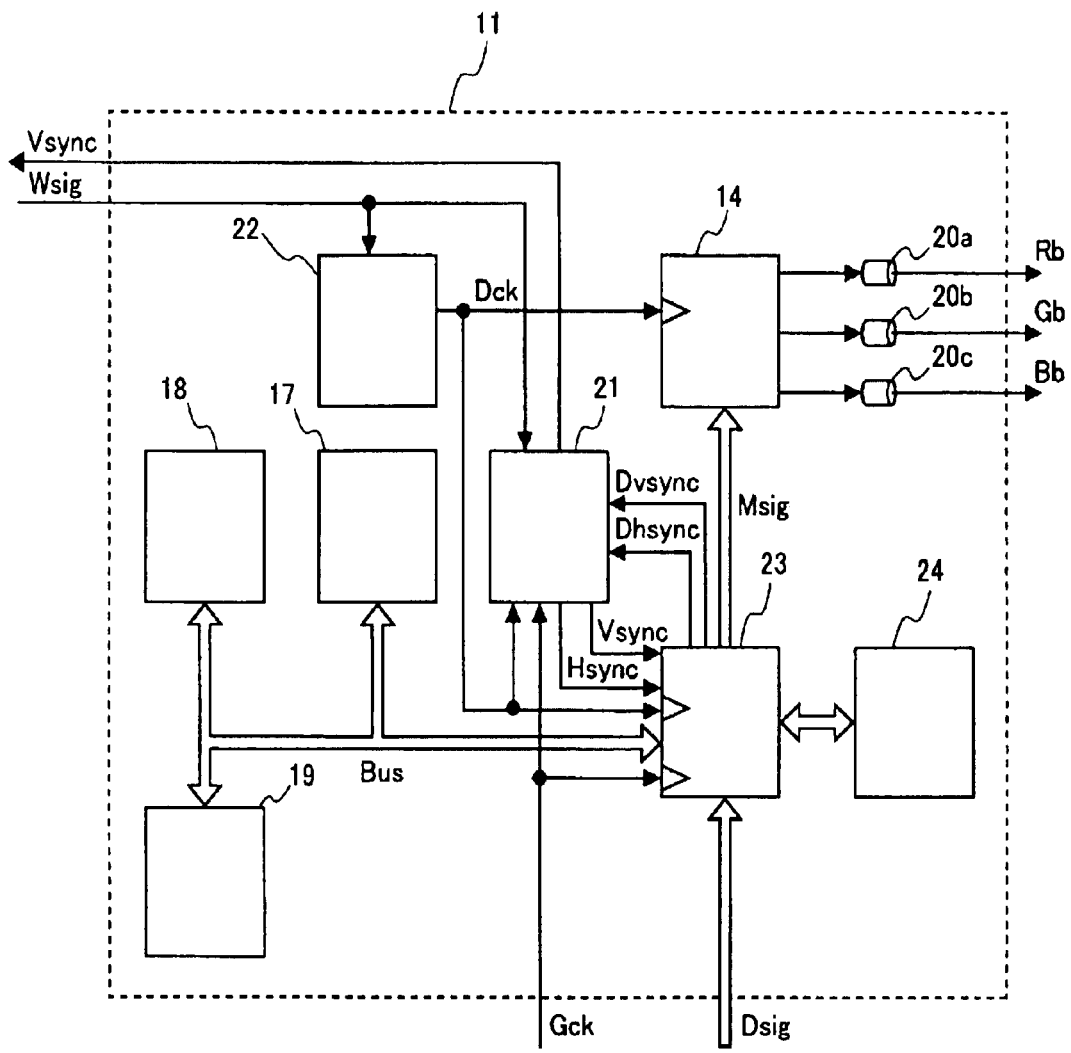
FIG. 2 is a block diagram of a light beam generating part.

The light beam generating part 11 includes, as shown in FIG. 2, a light beam modulator 14, an image converter 23, a buffer memory 24, a ROM 17, a RAM 18, a CPU (central processing unit) 19, the R laser 20a, the G laser 20b, the B laser 20c, a synchronizing signal generator 21 and the dot clock generator 22.

An image signal Dsig is, in the embodiment, inputted to the image converter 23 as a RGB component signal of parallel data which is constituted of a plurality of bits for every external clock Gck.

A data format of the image signal Dsig (see FIG. 4(G), FIG. 5(H)) is formed such that data corresponding to one horizontal scanning line is constituted of horizontal synchronizing signal data Dhsync, horizontal scanning row number data dsn (constituted of a plurality of data indicative of first to jth horizontal scanning row numbers as Dsn(1) to Dsn(j)), control data Dcon (constituted of a plurality of data, that is, "m" pieces of data from Dcon(1) to Dcon(m) used for control), dot data D (constituted of a plurality of, that is, "n" pieces of data from D(1) to D(n) for respective first to nth light spots formed on the retina 80b in the horizontal direction) and horizontal blanking data Dhb (constituted of a plurality of, that is, "g" pieces of data from Dhb(1) to Dhb(g)).

Here, as a value of the horizontal scanning row number data Dsn, in the respective horizontal scanning rows which are indicated by the horizontal scanning row number data Dsn(1) to the horizontal scanning row number data Dsn(j), the image signal Dsig is transmitted to the light beam generating part 11 repeatedly in order of one piece of horizontal synchronizing signal data Dhsync, one piece of horizontal scanning row number data Dsn, "m" pieces of control data Dcon, "n" pieces of dot data D and "g" pieces of horizontal blanking data Dhb.

Here, as the value of horizontal scanning row number data Dsn, in the dot data D which is included in rows indicated by the horizontal scanning row number data Dsn(1) to the horizontal scanning row number data Dsn(f), data to be displayed on the retina sob are written in the respective dot data D(1) to dot data D(n) for the respective rows.

On the other hand, in the dot data D which is included in rows indicated by the horizontal scanning row number data Dsn(f+1) to the horizontal scanning row number data Dsn(j), the vertical blanking data Dvb is written in the respective dot data D(1) to dot data D(n). Here, the total number of the vertical blanking data Dvb for one frame (a unit for constituting one screen formed by scanning) becomes (j−f−1)×n (pieces). Here, the horizontal blanking data Dhb and the vertical blanking data Dvb are signals which do not allow the R laser 20a, the R laser 20a and the R laser 20a to emit light and are provided for securing retracing time line in the horizontal scanning and the vertical scanning.

That is, one frame of the image signal Dsig is constituted of (1+1+m+n+g)×j (pieces) of data each of which is formed of a plurality of bits, and the number of data which actually modulates the brightness of the light spot is n×f (pieces).

Here, when the image signal Dsig is a signal based on another method, for example, a YIQ component signal in serial data for every one bit or the like, without separately inputting the external clock Gck, the external clock Gck is generated from the image signal Dsig using a phase-locked loop (PLL) (not shown in the drawing), and the YIQ component signal is converted into the ROB component signals in parallel in the embodiment using a format converter (not shown in the drawing). Further, to complete the scanning within one frame, the parallel data is converted from interlace scanning data into progressive scanning data, and the converted parallel data is inputted to the image converter 23 as the image signal Dsig together with the external clock Gck which is generated by the PLL.

The image converter 23 is connected to other blocks including the CPU 19 by way of a bus line BUS, has an intelligent function, and is controlled by the CPU (central processing unit) 19. Further, the image converter 23 also has a memory function of a dual-port-type FIFO (First Input First Out) type and is configured to transmit an image modulation signal Msig which is constituted of parallel data which modulates respective R laser, B laser and G laser to the light beam modulator 14 for every dot clock Dck unit.

The image converter 23 is controlled by the CPU 19 via the bus line Bus and also controls the buffer memory 24 for acquiring the image modulation signal Msig from the image signal Dsig.

The buffer memory 24 is provided for absorbing the difference in data processing speed (data transmission rate) between the external clock Gck and the dot clock Dck, wherein the larger the difference in the data processing speed (data transmission rate) between the external clock Gck and the dot clock Dck is, the larger a required capacity of the buffer memory 24 becomes.

In the embodiment, the difference in the data transmission rate between the external clock Gck and the dot clock Dck during one row scanning (scanning in the horizontal direction) period is configured to be absorbed in two stages. In the first stage, the difference in the data transmission rate is absorbed during a rear light beam stop period Tidl2 described later. In this case, it is sufficient for the buffer memory 24 to prepare a memory corresponding to n-pieces of dot data D which is a capacity of dot data D for one row. Further, in the second stage, the difference in the data transmission rate is absorbed during a vertical blanking period Tvblnk described later. In this case, it is sufficient for the buffer memory 24 to prepare a memory corresponding to a n×j pieces of dot data which is a capacity of dot data D for one frame.

To be more specific, when the data transmission rate based on the external clock Gck is larger than the data transmission rate based on the dot clock Dck due to a long resonance cycle Twsig described later, a rear-side light beam stop period Tidl2 is shortened, while when the data transmission rate based on the external clock Gck is smaller than the data transmission rate based on the dot clock Dck due to a short resonance cycle Twsig, a rear-side light beam stop period Tidl2 is extended thus absorbing the difference in the data transmission rate during the period by the buffer memory 24.

Further, when the data transmission rate is so different that the difference in data transmission rate cannot be absorbed within the one horizontal canning period, it is not possible to achieve the alignment of time processing within one row scanning time. Accordingly, when the resonance cycle Twsig is long, the vertical blanking period Tvblnk is shortened, while when the resonance cycle Twsig is short, the vertical blanking period Tvblnk is extended thus absorbing the difference in the data transmission rate during the period by the buffer memory 24.

The synchronizing signal generator 21 is provided for performing the processing in the light beam modulator 14 and for generating a signal which becomes a trigger for changing the direction of the light beam in the vertical scanning part 63b thus synchronizing positions of a light spot scanned on the retina 80b. That is, the synchronizing signal generator 21 is provided for forming a two-dimensional image on the retina 80b in synchronism with the position of the light spot in the horizontal direction and the position of the light spot in the vertical direction and the brightness of the R laser 20a, the G laser 20b and the 13 laser 20c.

The synchronizing signal generator 21 generates a vertical synchronizing signal Vsync for vertical synchronizing which is supplied to the vertical scanning part 63b, generates a vertical scanning reset signal Vreset which is supplied to the vertical scanning part 63b and, further, generates a gated dot clock Gdck which is outputted to the light beam modulator 14 and the image converter 23. The signals generated from the synchronizing signal generator 21 are generated based on horizontal synchronizing signal data Dhsync, vertical synchronizing signal data Dvsync from the image converter 23, and the dot clock Dck and a binarized oscillation signal Wsig from the dot clock generator 22.

The light beam modulator 14 controls the light emission brightness of the laser beams specified in response to an image modulation signal Msig for every one dot based on the dot clock Dck. The image modulation signal Msig is a signal which extracts only the dot data D from the image signal Dsig, and the dot data D is constituted of a plurality of bits and includes a signal indicative of information on the intensity of red (hereinafter, abbreviated as an R signal), a signal indicative of information on the intensity of green (hereinafter, abbreviated as a G signal) and a signal indicative of information on the intensity of blue (hereinafter, abbreviated as a B signal). Here, the light beam modulator 14 modulates the R laser 20a in response to a size of the R signal, the G laser 20b corresponding to a size of the G signal, and the B laser 20c corresponding to a size of the B signal.

The dot clock generator 22 generates the dot clock Dck which is a signal formed by multiplying the binarized oscillation signal Wsig. A phase-locked loop is used for the dot clock generator 22.

Figure 3:
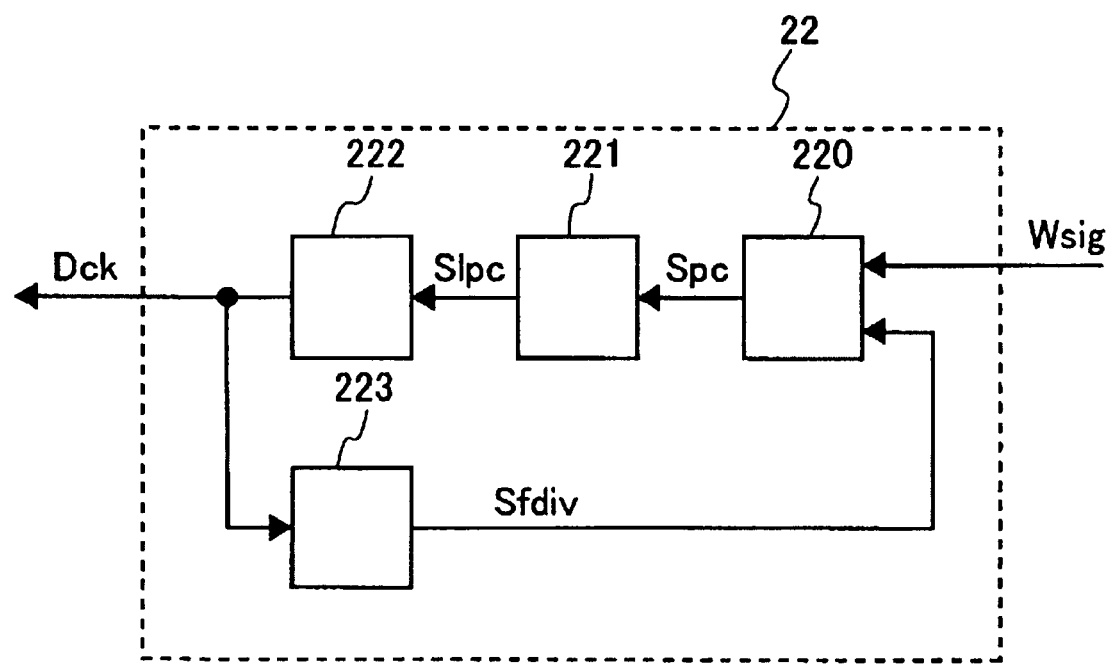
FIG. 3 is a block diagram of a phase-locked loop.

FIG. 3 shows one example of the phase-locked loop. In FIG. 3, a phase comparator 220 performs a phase comparison between the binarized oscillation signal Wsig and a frequency-divided frequency signal Sfdiv which is a signal formed by dividing the frequency of the dot clock Dck from a 1/N counter 223 in N and outputs a phase error signal Spc. A lag lead filter 221 performs phase compensation and gain compensation of the control loop and outputs a post-compensation phase error signal Slpc based on the phase error signal Spc so as to optimize the loop characteristics. A VCO (Voltage Controlled oscillator) 222 generates the dot clock having a frequency corresponding to the post-compensation phase error signal Slpc.

such a control loop performs a control such that that respective edge positions of the binarized oscillation signal Wsig and the frequency-divided frequency signal Sfdiv maintain a predetermined relationship therebetween and hence, the frequencies of the binarized oscillation signal Wsig and the frequency-divided frequency signal Sfdiv are completely agree with each other. Accordingly, the frequency of the dot clock Dck becomes a frequency obtained by multiplying the binarized oscillation signal Wsig N times.

The ROM (Read Only Memory) 17 and the RAM (Random Access Memory) 18 are connected to the bus line Bus, and the CPU 19 writes a progress of the processing into the RAM 18 or reads the progress of the processing from the RAM 18 in accordance with steps stored in the ROM 17.

Hereinafter, the summary of the manner of operation of the light beam generating part 11 is explained in accordance with a timing chart.

Figure 4:
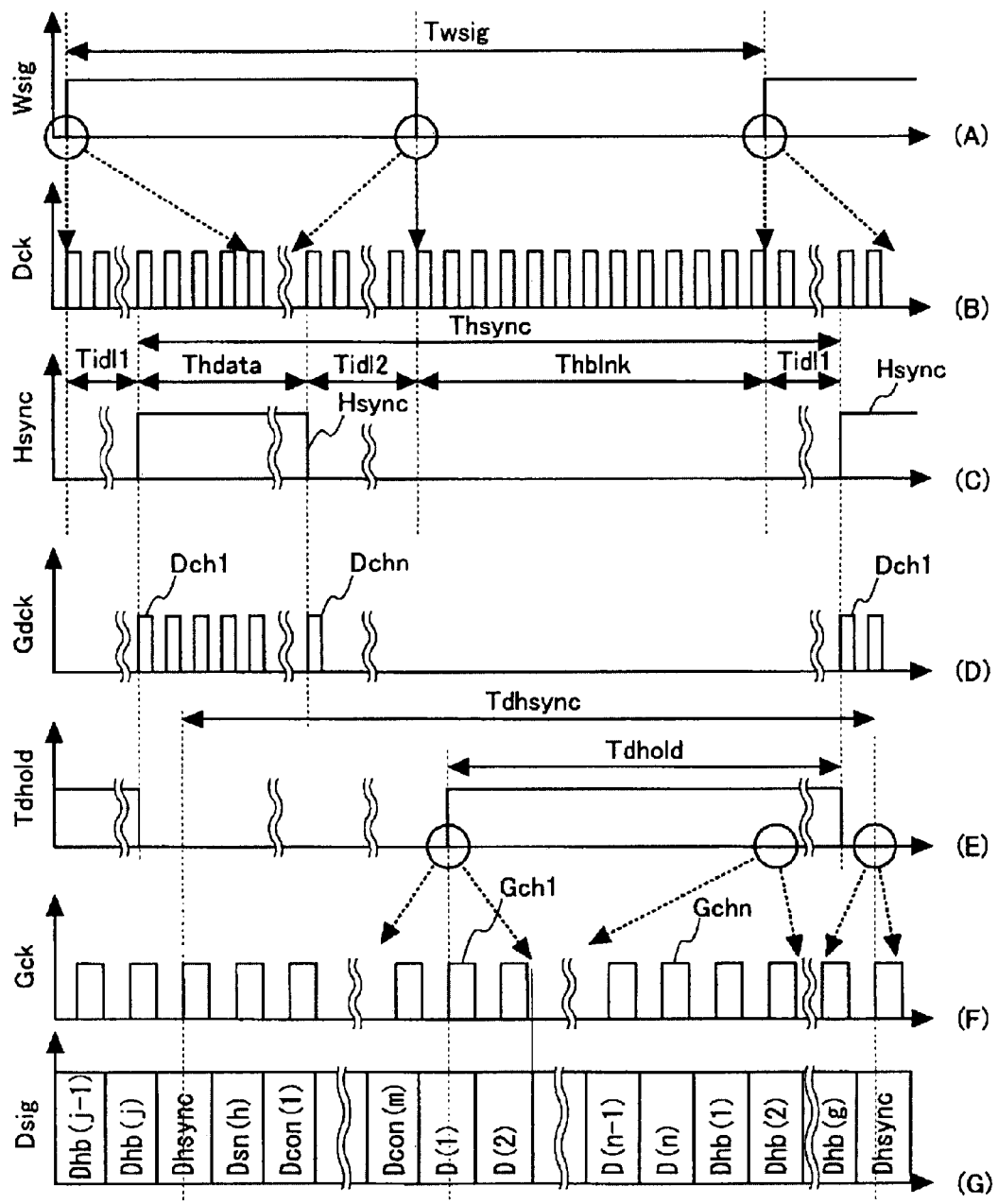
FIG. 4 is a view showing signals of respective portions of a horizontal scanning system.

FIG. 4 shows a timing chart relating to a horizontal scanning system. In FIG. 4(A) to FIG. 4(G), time "t" is taken on an axis of abscissas. FIG. 4(A) shows the binarized oscillation signal Wsig from the horizontal scanning part 63*a*, FIG. 4(B) shows a dot clock Dck generated by the phase-locked loop (PLL), FIG. 4(C) shows the horizontal synchronizing signal Hsync generated by the synchronizing signal generator 21, FIG. 4(D) shows the gated dot clock Gdck generated by the synchronizing signal generator 21. A data holding period Tdhold shown in FIG. 4(D) is a time in which the dot data D is held in a buffer memory 24 from the acquisition of the dot data D by the optical scanner 1 to the emission of laser beams by the light beam modulator 14. FIG. 4(F) shows the external clock Gck, and FIG. 4(G) shows the image signal Dsig. Here, views shown in FIG. 4(B) to FIG. 4(D) are partially enlarged views showing a time axis in the vicinity of a circular mark in an enlarged manner in FIG. 4(A), and views shown in FIG. 4(F) and FIG. 4(G) are partially enlarged views showing the time axis in the vicinity of the circular mark in FIG. 4(E) in an enlarged manner.

The summary of the respective signals described above are explained. The horizontal synchronizing signal Hsync is generated using the binarized oscillation signal Wsig as a reference. Accordingly, the movement of the horizontal reflecting mirror 8 which is oscillated at the resonance frequency, that is, the moving position of the light spot formed on the retina Bob by the light beams using the optical system in the horizontal direction and the horizontal synchronizing signal Hsync completely synchronize with each other. Here, the resonance cycle Twsig which constitutes one cycle time of the binarized oscillation signal Wsig becomes the inverse number of the resonance frequency of the movable member on which the horizontal reflecting mirror 8 is arranged.

When the light beams are radiated on the horizontal reflecting mirror 8, the direction of the light beams is changed. However, depending on the position of the horizontal reflecting mirrors, the linearity of the scanning is deteriorated. Accordingly, to stop the radiation of the laser beams at a portion where the linearity of the scanning is deteriorated during the resonance cycle Twaig, the horizontal synchronizing signal Hsync is configured to rise after a front-side light beam stop period Tidl1 (FIG. 4(C)) having a predetermined length passes after raising the binarized oscillation signal Wsig.

Further, during the resonance cycle Twsig, at a portion where the binarized oscillation signal Wsig assumes a high level (a level arranged at an upper portion in FIG. 4 being set as the high level), the light spot is scanned on the retina sob from right to left, while at a portion where the binarized oscillation signal Wsig assumes a low level, the scanning direction is inverted and hence, the light spot is scanned from left to right.

On the other hand, the image signal Dsig is expected to be scanned progressively only in one direction and hence, in FIG. 4(A), a horizontal blanking period Thblnk is provided so that the horizontal synchronizing signal Hsync assumes the high level only in a range of period in which the binarized oscillation signal Wsig assumes the high level which corresponds to a period in which the light spot is scanned from right to left. Further, the rear-side light beam stop period Tidl2 is provided to absorb the influence of the resonance cycle Twsig which varies corresponding to the movable member and also to stop the radiation of the laser beams at a portion where the linearity of the scanning is deteriorated.

Then, the horizontal synchronizing signal Hsync is lowered after a light beam radiation period Thdata 1 which constitutes a period when "n" pieces of the dot clocks Dck whose number is equal to the number of the dot data D which corresponds to one horizontal scanning of the image signal Dsig are counted elapses.

In response to this horizontal synchronizing signal Hsync, a gate is applied to the dot clock Dck and hence, the gated dot clock Gdck shown in FIG. 4(D) is generated.

In synchronism with this gated dot clock Gdck, the light beams are radiated. To be more specific, in synchronism with the gated dot clock Gdck, the image modulation signal Msig is transmitted to the light beam modulator 14 from the image converter 23, and the light beams are radiated from the R laser 20*a*, the G laser 20*b* and the B laser 20*c* for every one clock of the gated dot clock Gdck with intensity determined by the image modulation signal Msig.

Here, a plurality of dot data D which has been already acquired is aligned in the buffer memory 24 and hence, in synchronism with the rise of the gated dot clock Gdck which is arranged at a position indicated by symbol Dch1 (FIG. 4(D)), the image modulation signal Msig which corresponds to the dot data D(1) is transmitted to the light beam modulator 14 whereby the light beams radiated from the k laser 20*a*, the G laser 20*b* and the B laser 20*c* are modulated. Further, in synchronism with the rise of the next gated dot clock Gdck, the image modulation signal Msig which corresponds to the dot data D(2) is transmitted to the light beam modulator 14 and hence, the beams radiated from the R laser 20*a*, the G laser 20*b* and the 8 laser 20*c* are modulated. Finally, in synchronism with the rise of the gated dot clock Gdck, the image modulation signal Msig which corresponds to symbol Dchn (FIG. 4(D)) is transmitted to the light beam modulator 14 and hence, the light beams radiated from the R laser 20*a*, the G laser 20*b* and the B laser 20*c* are modulated whereby one row of the horizontal scanning is completed.

Here, when the scanning of one specific row is completed, after a horizontal synchronizing period Thsync elapses, the horizontal synchronizing signal Hsync is again generated, and the scanning of the next row is started.

FIG. 4(E) shows a concept how the dot data D is stored in the buffer memory 24. When the difference between the data transmission rate of the image modulation signal Msig by the gated dot clock Gdck and the data transmission rate of the image signal Dsig in response to the external clock is small, a data holding period Tdhold is shortened, while when the difference between the data transmission rate of the image modulation signal Msig in response to the gated dot clock Gdck and the data transmission rate of the image signal Dsig in response to the external clock is large, the data holding period Tdhold is extended.

The data transmission rate of the image modulation signal Msig in the horizontal scanning is defined based on the resonance cycle Twsig. However, the data transmission rate of the image signal Dsig is defined based on the external clock Gck which is generated by the external device and hence, for example, when the data transmission rate of the image modulation signal Msig is exceedingly smaller than the data transmission rate of the image signal Dsig, there arises a drawback that, while the light spot is scanned in the horizontal direction, the image signal Dsig which cannot be displayed as the light spot is stored one after another. In such a case, the data holding period Tdhold soon becomes equal to or longer than the horizontal synchronizing period Thsync and hence, the data holding period Tdhold with respect to the image signal Dsig which is acquired thereafter is added in a cumulative manner and is increased.

However, when the data holding period Tdhold has a length which can be reset during the vertical blanking period Tvblnk, the reproduction of the two-dimensional image by the light spot is not delayed and can be continuously performed thereafter without interruption.

FIG. 4(F) and FIG. 4(G) show timings at which the image signal Dsig is decoded. The image signal Dsig shown in FIG. 4(G) is decoded for every external clock Gck shown in FIG. 4(F).

Here, the dot data D(1) (indicated by symbol D(1) in FIG. 4(G)) is sampled in response to the external clock Gck indicated by symbol Gch1 (FIG. 4(F)) and is held in a region to store the dot data D(1) in the buffer memory 24 during the data holding period Tdhold. Here, in response to the gated dot clock Gdck indicated by the symbol Dch1 (FIG. 4(D)) on the right side, the image modulation signal Msig is transmitted to the light beam modulator 14 from the image converter 23.

Here, the explanation is made with respect to how the dot data D(1) is specified by the image signal Dsig. The horizontal synchronizing signal data Dhsync has a particular bit arrangement (a unique pattern) which is distinguished from the horizontal scanning row number data Dsn, the control data Dcon, the dot data D and the horizontal blanking data Dhb and hence, it is possible to easily sample the horizontal synchronizing signal data Dhsync. In this manner, by specifying a position of the horizontal synchronizing signal data Dhsync in the image signal Dsig which is continuously inputted into the optical scanner 1, it is possible to specify the positions of the horizontal scanning row number data Dsn and the position of the dot data D whose arrangements are preliminarily specified. Then, the buffer memory 24a can acquire the number of the horizontal scanning row and contents of the dot data D(1) to the dot data D(n) in the row therein.

In FIG. 4(G), symbol Dhsync indicates the horizontal synchronizing signal data, and Symbol Dsn(h) indicates that the scanning row number is "hth". Further, symbol Dcon(1) and the like indicate "m" pieces of data which are used for the above-mentioned control, symbol D(1) and the like indicate dot data D constituted of "n" pieces of dot data, and symbol Dhb(1) and the like indicate the horizontal blanking data Dhb.

The length of the horizontal synchronizing period Thsync shown in FIG. 4(C) and the length of the horizontal synchronizing signal data period Tdhsync do not agree with each other, and the length of one cycle of the dot clock Dck shown in FIG. 4(B) and one cycle of the external clock Gck shown in FIG. 4(F) do not agree with each other. However, both the number of the dot clocks Dak which are present during a period from a clock indicated by the symbol Dch1 to a clock indicated by the symbol Dchn and the number of the external clocks Gck which are present during a period from a clock indicated by the symbol Gch1 to a clock indicated by the symbol Gchn are "n" and agree with each other and hence, the number of data used for scanning the light spot in the horizontal direction is just sufficient, and the difference between the data transmission rate of the image signal Dsig and the data transmission rate of the image modulation signal Msig is absorbed by the buffer memory 24 which stores the dot data D during the data holding period Tdhold.

To summarize the above-described description, the dot data D(1) to the dot data D(n) are arranged in a predetermined portion of the buffer memory 24 by the image converter 23. Here, a control is performed such that the first dot data D(1) which corresponds to a right end to the nth dot data D(n) are sequentially transmitted to the light beam modulator 14 for every dot clock Dck.

As mentioned above, the explanation of the summary of operation has been made heretofore with respect to the horizontal synchronizing system. However, it is difficult to obtain a desired image on the retina 80b unless the vertical synchronization is performed in the vertical direction. A vertical synchronizing signal Vsync is generated in the synchronizing signal generator 21 such that a position of the light spot on the retina 80b in the vertical direction and data to be displayed by an image signal Dsig are aligned with each other.

Figure 5:
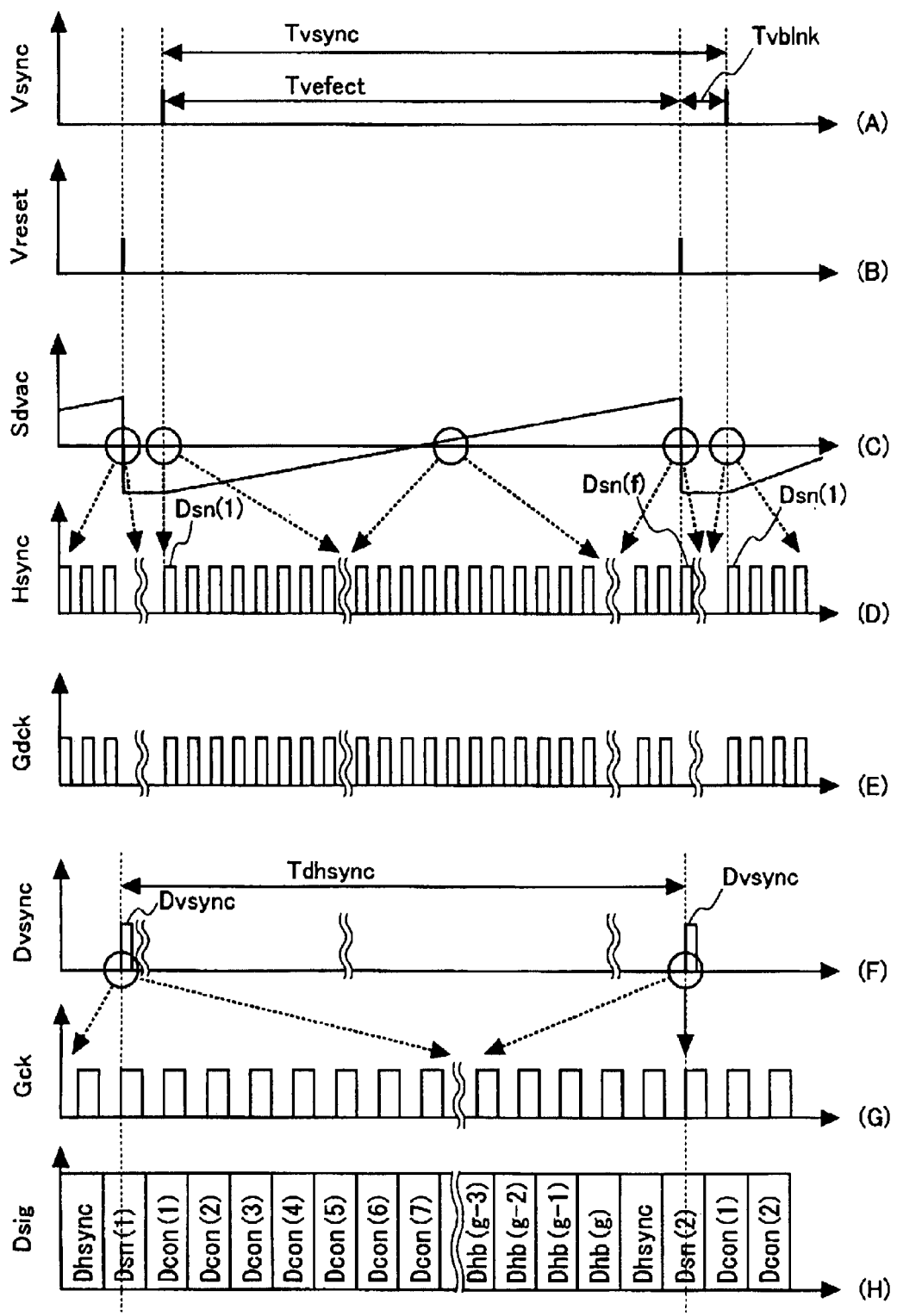
FIG. 5 is a view showing signals of respective portions of the vertical scanning system.

A timing chart with respect to the vertical synchronizing system is shown in FIG. 5. Respective axes of abscissas in FIG. 5(A) to FIG. 5(H) represent time t.

FIG. 5(A) shows a vertical synchronizing signal Vsync which is outputted from the synchronizing signal generator 21 to a vertical scanning part 63b, FIG. 5(B) shows a vertical scanning reset signal Vreset which is outputted from the synchronizing signal generator 21 to the vertical scanning part 63b, FIG. 5(C) shows a vertical drive signal Sdvac which is generated in the vertical scanning part 63b based on the vertical synchronizing signal Vsync and the vertical scanning reset signal Vreset and drives a Galvano reflecting mirror 210, FIG. 5(D) shows a horizontal synchronizing signal Hsync which is generated in the synchronizing signal generator 21, FIG. 5(E) shows a gated dot clock Gdck (contents of black frames representing "n" pieces of dot clocks Dck), FIG. 5(F) shows a vertical synchronizing signal data Dvsync which is formed in an image converter 23, FIG. 5(G) shows an external clock Gck, and FIG. 5(H) shows an image signal Dsig. Here, FIG. 5(D) and FIG. 5(F) are views of waveforms obtained by partially enlarging a time axis in the vicinity of circle marks in FIG. 5(C), and FIG. 5(G) and FIG. 5(H) are views of waveforms obtained by partially enlarging a time axis in the vicinity of circle marks in FIG. 5(F).

That is, at the rise of the vertical synchronizing signal Vsync shown in FIG. 5(A), the Galvano reflecting mirror 210 is controlled to form an image of a light spot on a right upper end portion of the retina 80b, and, at the same time, an image modulation signal Msig corresponding to a position of the light spot is transmitted from the image converter 23 to a light beam modulator 14, and in the light beam modulator 14, an R laser 20a, a G laser 20b and a B laser 20c respectively emit light with light emission luminances corresponding to the image modulation signal Msig (dot data D corresponding to a right upper end position). Then, the light spot is scanned from right to left in the horizontal direction thereafter, and, at the same time, the light spot is scanned from top to bottom. Hereinafter, processes of generating the vertical synchronizing signal VSync and the vertical scanning reset signal Vreset are explained.

FIG. 5(H) shows a portion of the image signal Dsig. A content of the image signal Dsig shown in FIG. 5(H) is read by the image converter 23 based on the external clock Gck shown in FIG. 5(G). Here, the image converter 23 detects a horizontal synchronizing signal data Dsync and specifies the alignment of the image signal Dsig. Further, the image converter 23 reads a content of horizontal scanning row number data Dsn and when the content of the horizontal scanning row number data Dsn is indicative of a first row number (indicated by symbol Dsn (1) in FIG. 5(H)), the vertical synchronizing signal data Dvsync is generated by the image converter 23.

Further, the dot data D(1) to the dot data D(n) whose positions to be displayed as light spots in one frame by the vertical synchronizing signal data Dvsync are arranged in a predetermined position of the buffer memory 24. In this manner, the dot data from the first dot data D(1) in the first row corresponding to a right upper end to the nth dot data D(n) in the fth row are ready to be transmitted to the light beam modulator 14 sequentially as the image modulation signal Msig for every dot clock Dck.

Further, the vertical synchronizing signal data Dvsync is transmitted to the synchronizing signal generator 21 at the timing shown in FIG. 5(F).

Then, a signal outputted in synchronism with the vertical synchronizing signal data Dvsync with the rise of the horizontal synchronizing signal Hsync is the vertical synchronizing signal Vsync shown in FIG. 5(A). Here, since the horizontal synchronizing signal Hsync is synchronized with the rises of the gated dot clock Gdck and the dot clock Dck, the rise of the vertical synchronizing signal vsync is also synchronized with the rise of the gated dot clock Gdck and the dot clock Dck.

In synchronism with the rise of such a vertical synchronizing signal Vsync, a voltage value of the vertical drive signal Sdvac shown in FIG. 5(C) is increased with a fixed gradient. Then, the vertical drive signal Sdvac is applied to the Galvano reflecting mirror 210 to start scanning in the vertical direction. Thereafter, when the number of the horizontal synchronizing signal Hsync reaches f pieces (the number of the gated dot clock Gdck being f×n pieces), the transmission of the horizontal synchronizing signal Hsync and the transmission of the gated dot clock Gdck are stopped, the vertical scanning reset signal Vreset shown in FIG. 5B is generated, and the vertical drive signal Sdvac returns again to the voltage at the time of starting the vertical scanning and the operation waits for the starting of scanning in the vertical direction for a next frame. Here, a time which elapses until the number of the horizontal synchronizing signal Hsync reaches f pieces (the number of the gated dot clock Gdck being f×n pieces) is defined as an effective vertical scanning period Tvefect. A sum of a vertical blanking period Tvblnk and the effective vertical scanning period Tvefect becomes a vertical scanning period Tvsync. A method of generating the vertical drive signal Sdvac is described later.

Here, the vertical scanning period Tvsync which is a period from the rise of a vertical synchronizing signal Vsync to the rise of the next vertical synchronizing signal Vsync and a vertical inter-scanning-data period Tdvsync which is a period from the horizontal scanning row number data Dsn to the next horizontal scanning row number data Dsn in the image signal Dsig agree with each other within one-clock accuracy of the dot clock Dck.

Here, a scanning speed of the Galvano reflecting mirror 210 for scanning the light spot on the retina 80b in the vertical direction is slow compared to a scanning speed of the horizontal reflecting mirror 8 and hence, it is possible to achieve a desired control of the Galvano reflecting mirror 210 in response to the vertical drive signal Sdvac whereby, different from the horizontal reflecting mirror 8, no problem a rises in controlling the Galvano reflecting mirror 210 based on the vertical drive signal Sdvac.

Here, a length of the vertical blanking period Tvblnk is relevant to a length of a resonance cycle Twsig. When the resonance cycle Twsig is so long that the difference between a data transfer rate of the image signal Dsig and a data transfer rate of the image modulation signal Msig cannot be absorbed with in every one horizontal synchronizing period Thsync, the difference in data transfer rate is absorbed by the vertical blanking period Tvblnk.

For example, when the data transfer rate of the image modulation signal Msig is small, after completion of scanning of the light spot for one frame, the image signal Dsig of the next frame comes in a short period of time thus shortening the length of the vertical blanking period Tvblnk.

On the other hand, when the data transfer rate of the image modulation signal Msig is large, the image signal Dsig of the next frame comes when a longer period of time elapses after completion of scanning of the light spot for one frame. In this manner, even when the length of the resonance cycle Twsig varies, the difference between the data transfer rate of the image modulation signal Msig and the data transfer rate of the image signal Dsig generated by the variation of the resonance cycle Twsig in the inside of the optical scanner 1 can be absorbed by a buffer memory 24.

To summarize the above, in the present embodiment, the rise of the gated dot clock Gdck and the rise of the horizontal synchronizing signal Hsync are synchronized with each other and further, the rise of the horizontal synchronizing signal Hsync and the rise of the vertical synchronizing signal Vsync are synchronized with each other. Still further, at the rise of the gated dot clock Gdck immediately after the rise of the vertical synchronizing signal Vsync, the dot data D(1) corresponding to the first dot data in the first row arranged in the buffer memory 24 is transmitted to the light beam modulator 14 thus allowing the R laser 20a, the G laser 20b and the B laser 20c to emit light beams. Sequentially, thereafter, data is read from the buffer memory 24 based on the gated dot clock Gdck and is transmitted to the light beam modulator 14 thus allowing the R laser 20a, the G laser 20b and the B laser 20c to emit light beams. As a result, it is possible to make the timing of light emission and the position of the light spot composed of three laser lights from the R laser 20a, the G laser 20b and the B laser 20c formed on the retina 80b agree with each other.

By adopting such a synchronizing method, the present invention is not limited to the image signal Dsig having the format of RGB components explained in conjunction with this embodiment and is also applicable to signals of various formats used in general (for example, an NTSC composite, NTSC components, other RGB components, a MUSE, a ISDB, a DVD or the like).

Further, the optical scanner 1 includes the horizontal scanning part 63a and the vertical scanning part 63b. The horizontal scanning part 63a has a function of scanning the light spot on the retina 80b horizontally by changing the radiation direction of the light beam. The horizontal scanning part 63a also includes an oscillation-type horizontal optical scanning mechanism 130 which constitutes an oscillation-type optical scanning mechanism for horizontally scanning the light spot on the retina 80b, a horizontal drive signal generator 30 (see FIG. 8) which is a drive signal generator for supplying a drive signal to the oscillation-type horizontal optical scanning mechanism 130, and an oscillation signal generator 40 (see FIG. 8). The oscillation-type horizontal optical scanning mechanism 130 also includes the horizontal reflecting mirror 8 (see FIG. 6) which constitutes a portion of the optical path part. Here, the oscillation signal generator 40 also includes, as mentioned previously, the oscillation-type optical scanning mechanism having the second resilient member and the detection piezoelectric element.

The oscillation-type horizontal optical scanning mechanism 130 oscillates, for scanning the light spot on the retina 80b in the horizontal direction, the movable member which mounts the horizontal reflecting mirror 8 for reflecting the light beam to change the radiation direction of the light beam thereon. In this embodiment, the oscillation-type horizontal optical scanning mechanism 130 allows the movable member to resonate. Due to the resonation of the movable member, the horizontal reflecting mirror a can obtain large amplitude of oscillation. By making use of this resonance, it is possible to largely change the radiation direction of the light beam using the miniaturized oscillation-type horizontal optical scanning mechanism 130.

Figure 6:
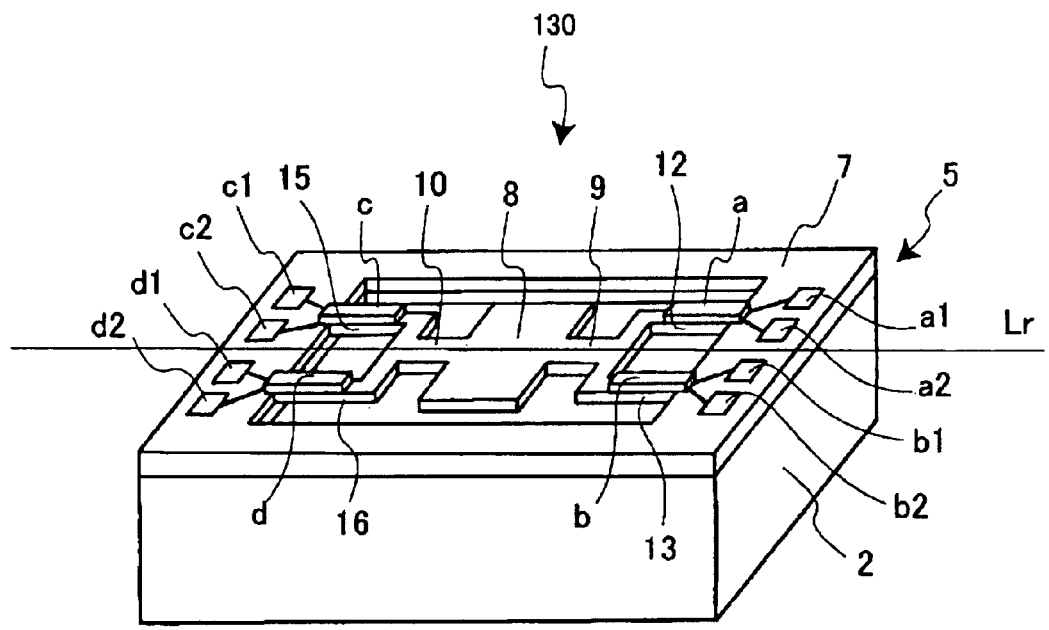
FIG. 6 is a view of an oscillation-type horizontal optical scanning mechanism.

FIG. 6 is a perspective view of the oscillation-type horizontal optical scanning mechanism 130. The oscillation-type horizontal optical scanning mechanism 130 includes the base platform 2 having an approximately rectangular parallelepiped shape, and a recessed portion is formed in the base platform 2 such that the recessed portion opens at a center portion of an upper surface of the base platform 2. A vibrator 5 is fixedly mounted on the upper surface of the base platform 2. The base platform 2 is fixedly mounted on an appropriate portion of the optical scanner d1.

The vibrator 5 includes a fixing frame portion 7 and the fixing frame portion 7 is supported on the upper surface of the base platform 2. Since the recessed portion which opens at the upper surface of the base platform 2 is formed in the base platform, at the time of oscillations (vibrations) of the horizontal reflecting mirror 8 formed on the vibrator 5, it is possible to prevent the horizontal reflecting mirror 8 from interfering with the base platform 2. The base platform 2 is configured to have a fine size and the recessed portion is formed by etching, for example.

The vibrator 5 is formed using a small thin silicon plate having an approximately rectangular shape in a plan view as a substrate. A plurality of constitutional elements of the vibrator 5 is formed on the silicon plate. These constitutional elements include the horizontal reflection mirror 8, a first resilient member which is connected to the horizontal reflection mirror 8 and is constituted of plate-shaped resilient member 9, resilient member 12 and resilient member 13, a second resilient member which is connected to the horizontal reflection mirror 8 and is constituted of plate-shaped resilient member 10, resilient member 15 and resilient member 16, and a fixed frame portion 7 to which the resilient member 12, the resilient member 13, the resilient member is and the resilient member 16 are respectively connected. Here, among the constitutional elements of the vibrator 5, the horizontal reflecting mirror 8, the first resilient member and the second resilient member constitute movable members which are movable relative to the fixed frame portion 7 which is fixed to the optical scanner 1.

These constitutional elements are formed on the silicon plate by etching. In this embodiment, the vibrator 5 is integrally formed of these constitutional elements.

As shown in FIG. 6, the horizontal reflecting mirror 8 has a rectangular or square shape and is arranged at an approximately center portion of the vibrator 5. The horizontal reflecting mirror 8 is oscillated about an oscillation axis Lr which extends in the lateral direction in FIG. 6 to change the reflection direction of light incident on the horizontal reflecting mirror 8.

In the vibrator 5, on one side of the horizontal reflecting mirror 8, two resilient members, that is, the resilient member 12 and the resilient member 13 are bifurcated in parallel to each other from the resilient member 9. In the same manner, on another side of the horizontal reflecting mirror 8, two resilient members, that is, the resilient member 15 and the resilient member 16 are bifurcated in parallel to each other from the resilient member 10. Here, the first resilient member which is constituted of the resilient member 9, the resilient member 12 and the resilient member 13 and the second resilient member which is constituted of the resilient member 10, the resilient member 15 and the resilient member 16 are arranged at positions which are symmetrical with respect to the horizontal reflecting mirror 8 sandwiched therebetween.

In the first resilient member, both two resilient members consisting of the resilient member 12 and the resilient member 13 are arranged at one side of the horizontal reflecting mirror 8 and face each other with the oscillation axis Lr therebetween. In the same manner, in the second resilient member, both two resilient members consisting of the resilient member 15 and the resilient member 16 are arranged at another side of the horizontal reflecting mirror 8 and face each other with the oscillation axis Lr therebetween. A driving piezoelectric element "a" and a driving piezoelectric element "b" are respectively fixedly mounted on the resilient member 12 and the resilient member 13 which belong to the first resilient member. On the other hand, a detection piezoelectric element "c" and a detection piezoelectric element "d" are respectively fixedly mounted on the resilient member 15 and the resilient member 16 which belong to the second resilient member.

The driving piezoelectric element "a", the driving piezoelectric element "b", the detection piezoelectric element "c" and the detection piezoelectric element "d" are respectively formed in a thin plate shape and are adhered to one-side surfaces of the resilient member 12, the resilient member 13, the resilient member 15 and the resilient member 16. The driving piezoelectric element "a", the driving piezoelectric element "b", the detection piezoelectric element "a" and the detection piezoelectric element "d" respectively have the same structure and each piezoelectric element is sandwiched by an upper electrode and a lower electrode in the direction perpendicular to the adhering surface.

Further, the upper electrode and the lower electrode of the driving piezoelectric element "a" are respectively connected with an input terminal a1 and an input terminal a2 which are mounted on the fixed frame portion 7 via lead lines, the upper electrode and the lower electrode of the driving piezoelectric element "b" are respectively connected with an input terminal b1 and an input terminal b2 which are mounted on the fixed frame portion 7 via lead lines, the upper electrode and the lower electrode of the detection piezoelectric element "c" are respectively connected with an output terminal c1 and an output terminal c2 which are mounted on the fixed frame portion 7 via lead lines, and the upper electrode and the lower electrode of the detection piezoelectric element "d" are respectively connected with an output terminal d1 and an output terminal d2 which are mounted on the fixed frame portion 7 via lead lines.

In this embodiment, the pair of driving piezoelectric element "a" and the driving piezoelectric element "b" respectively function as drive sources, generate the twisting vibrations around the oscillation axis Lr thus oscillating the horizontal reflecting mirror 8. Accordingly, when a voltage is applied between the upper electrode and the lower electrode of the respective driving piezoelectric element "a" and driving piezoelectric element "b", a displacement in the direction perpendicular to the voltage applying direction, that is, in the longitudinal direction is generated in the driving piezoelectric element "a" and the driving piezoelectric element "b" and this displacement is transmitted to the resilient member 12 and the resilient member 13.

Figure 7:
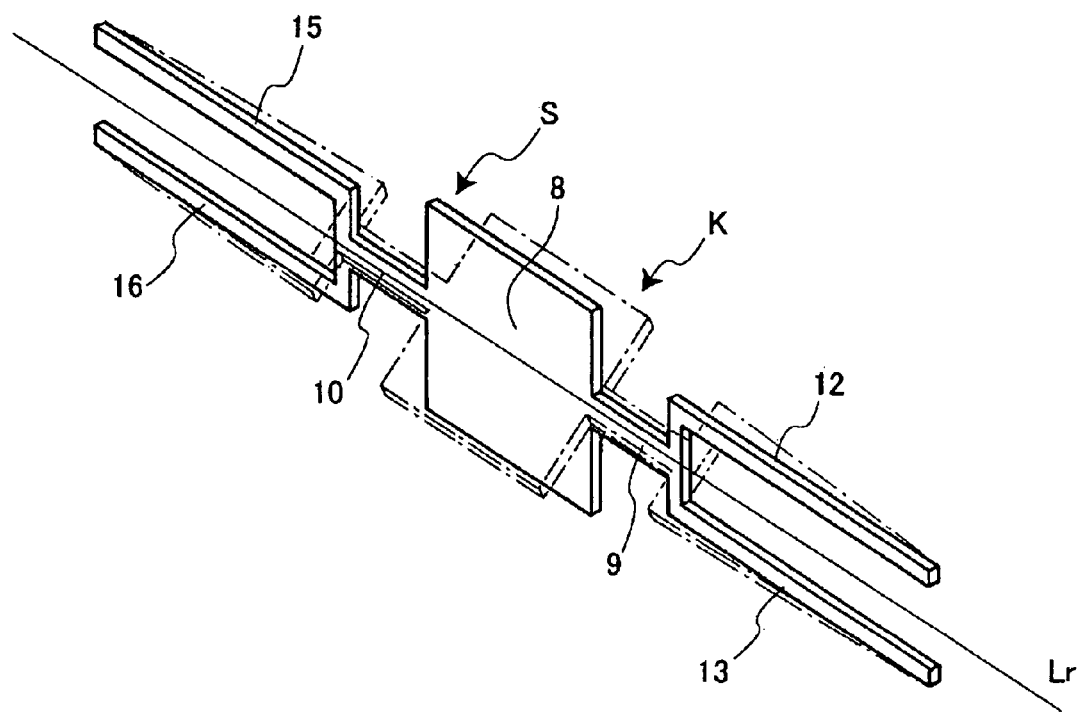
FIG. 7 is a view explaining a motion of movable members.

Due to this displacement, as shown in FIG. 7, the bending of the first resilient member is generated. This bending is performed using a connection portion of the first resilient member with the fixed frame portion 7 as a fixed end and a connection portion of the first resilient member with the horizontal reflecting mirror a as a free end. As a result, the free end of the first resilient member is displaced upwardly or downwardly depending on whether the bending direction of the first resilient member is upward or downward.

Then, due to two driving piezoelectric elements, that is, the driving piezoelectric element "a" and the driving piezoelectric element "b" which forms a couple, the free ends of the resilient member 12 and the resilient member 13 are bent to be deflected in the directions opposite to each other. As a result, the horizontal reflecting mirror 8 is, as shown in FIG. 7, rotated about the oscillation axis Lr. Here, to generate the oscillating motion of the horizontal reflecting mirror 8 about the oscillation axis Lr, an AC voltage is alternately applied to two driving piezoelectric elements, that is, the driving piezoelectric element "a" and the driving piezoelectric element "b" with phases reversed from each other.

To recapitulate the above, the resilient member 12 and the resilient member 13 have a function of converting the linear displacement of two driving piezoelectric elements, that is, the driving piezoelectric element "a" and the driving piezoelectric element "b" which are adhered to the resilient member 12 and the resilient member 13 into the bending motion and also have a function of converting the bending motion of the driving piezoelectric element "a" and the driving piezoelectric element "b" into the rotational motion of the resilient member 9. Due to this rotational motion of the resilient member 9, the horizontal reflecting mirror 8 is rotated. In this manner, by using the piezoelectric element as a drive source which biases the spring, it is possible to easily miniaturize the device.

In FIG. 7, a solid line shows positions of the first resilient member, the second resilient member, the horizontal reflecting mirror 8 when a voltage is not applied to the driving piezoelectric element "a" and the driving piezoelectric element "b" (indicated by symbol S). Further, a broken line shows positions of the first resilient member, the second resilient member, the horizontal reflecting mirror 8 when an AC voltage is applied to the driving piezoelectric element "a" and the driving piezoelectric element "b" (indicated by symbol K).

Another side of the horizontal reflecting mirror 8 is connected to the resilient member 10 which constitutes the second resilient member and is further connected to the fixed frame portion 7 by way of the bifurcated resilient member 15 and resilient member 16. Due to such a constitution, the respective portions of the second resilient member are also displaced due to the displacement generated in the horizontal reflecting mirror 8, wherein the resilient member 10 is displaced approximately in the same manner as the resilient member 9 using the oscillation axis Lr as a center axis, the resilient member 15 is displaced approximately in the same manner as the resilient member 12, and the resilient member 16 is displaced approximately in the same manner as the resilient member 13.

Since the detection piezoelectric element "c" and the detection piezoelectric element "d" are adhered to the resilient member 15 and the resilient member 16, when the bending motion is generated in the resilient member 15 and the resilient member 16, a signal corresponding to a twisting quantity of the second resilient member is obtained from an output terminal d1 and an output terminal d2. In this manner, it is possible to eventually obtain an oscillation signal Swsig described later. By using the piezoelectric element for generating the signal corresponding to the twisting quantity of the second resilient member, the miniaturization of the device can be realized.

Further, by using the piezoelectric element as the drive source of the first resilient member and by using the piezoelectric element having the same structure as the above-mentioned piezoelectric element as the detection sensor which detects the twisting quantity of the second resilient member, the structure of the movable members of the oscillation-type horizontal optical scanning mechanism 130 becomes completely symmetrical with respect to the oscillation axis Lr or the horizontal reflecting mirror B and the resonance frequency also becomes stable.

Although the first resilient member (constituted of the resilient member 9, the resilient member 12 and the resilient member 13), the second resilient member (constituted of the resilient member 10, the resilient member 15 and the resilient member 16), and the horizontal reflecting mirror B are movable members which are movable relative to the fixed frame portion 7, various resonance modes of these movable members are considered. As one of the resonance modes, there exists torsional resonance which uses the oscillation axis Lr as the center axis. To express the motion of the movable members under this resonance mode using an equation of motion, the motion becomes a so-called second-order system and provides a resonance system which resonates at an intrinsic resonance frequency.

Q(Quality Factor) of this resonance system amounts to several hundreds and a width of mesial magnitude is extremely small. Accordingly, when the AC voltage is applied to two driving piezoelectric elements, that is, the driving piezoelectric element "a" and the driving piezoelectric element "b", at a frequency of the AC voltage which agrees with the resonance frequency when the frequency is changed, amplitude of the oscillation of the movable member including the horizontal reflecting mirror a is extremely increased when the movable member is oscillated at the resonance frequency in such a manner, electric power supplied to the driving piezoelectric element "a" and the driving piezoelectric element "b" is also small and hence, it is possible to obtain the displacement of the horizontal reflecting mirror 8 which cannot be usually obtained whereby power efficiency can be largely enhanced and, at the same time, the miniaturization of the oscillation type horizontal optical scanning mechanism 130 can be realized.

However, the resonance frequency is changed corresponding to temperature or moisture of an environment in which the oscillation type horizontal optical scanning mechanism 130 is arranged, and the individual difference exists for every oscillation type horizontal optical scanning mechanism 130. On the other hand, as described previously, Q of the resonance system is high, that is, several hundreds and hence, the resonance frequency falls within an extremely small limited range whereby it is extremely difficult to make the frequency of the AC voltage generated by a drive signal generator and the resonance frequency completely agree with each other.

Figure 8:
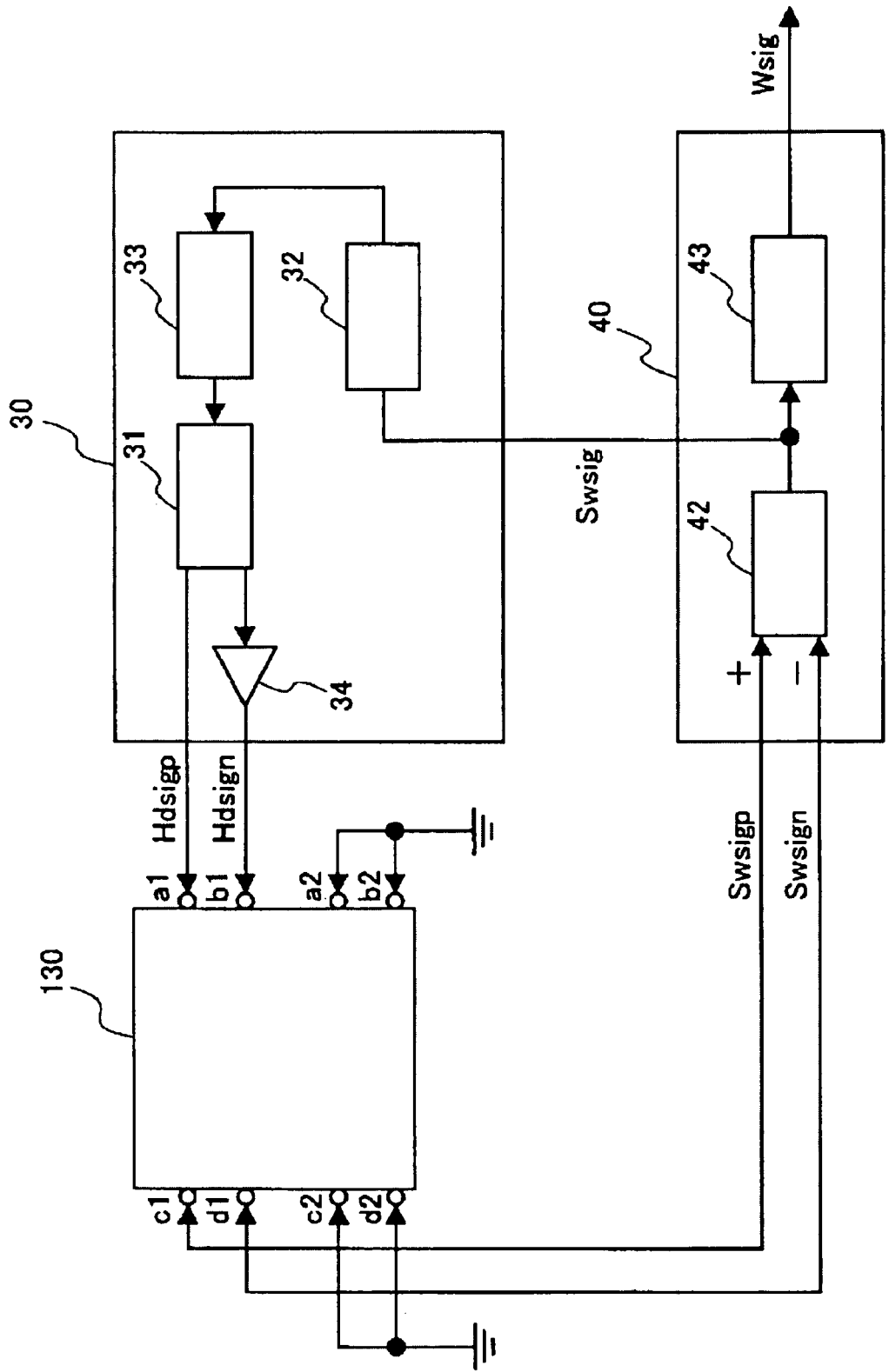
FIG. 8 is a block diagram of the horizontal scanning system.

As shown in FIG. 8, in this embodiment, a system which is formed by combining the horizontal drive signal generator 30, the oscillation signal generator 40 and the oscillation type horizontal optical scanning mechanism 130 constitutes a feedback system. This feedback system constitutes, when predetermined conditions are satisfied, a positive feedback system and performs the self-excited oscillation.

In this embodiment, the horizontal drive signal generator 30 generates the drive signal of the AC voltage which agrees with the resonance frequency of the movable member while performing the self-excited oscillation. Here, the drive signal generator is not limited to the drive signal generator of this embodiment provided that the drive signal generator outputs the AC voltage of the frequency which agrees with the resonance frequency of the movable member of the oscillation-type horizontal optical scanning mechanism 130.

For example, the drive signal generator may be constituted as follows. While shifting the frequency of the drive signal from the horizontal drive signal generator little by little, an oscillation signal corresponding to a displacement quantity of the movable member is detected. A frequency of the drive signal is continuously changed such that amplitude of the oscillation signal is increased, and a frequency which makes the amplitude of the oscillation signal assume a largest value is always sought. Using such a frequency as the center frequency, the frequency is changed slightly in the vicinity of the center frequency.

In FIG. 8, the horizontal drive signal generator 30 includes an amplifier 31, an AGC circuit (Auto Gain Control Circuit) 32, a phase shift circuit 33 and an inverting amplifier 34, while the oscillation signal generator 40 includes an adder 42 and a comparator 43.

An output terminal of the amplifier 31 is connected to an input terminal a1 of the horizontal drive signal generator 30, an output terminal of the inverting amplifier 34 is connected to an input terminal b1 of the horizontal drive signal generator 30, and a drive signal Hdsigp and a reverse phase drive signal Hdsign which have phases thereof reversed from each other (phases being inverted by 180° from each other) are inputted to the input terminal a1 and the input terminal b1. The input terminal a2 and the input terminal b2 are grounded.

A gain is automatically set in the AGC circuit 32 such that the amplitude of the oscillation signal Swsig assumes a predetermined amplitude, while in the phase shift circuit 33, for example, a phase of the oscillation signal Swsig is adjusted by an RC circuit consisting of a resistance and a capacitor.

Further, a positive-polarity oscillation signal Swsigp from an output terminal c1 is inputted to an input terminal of the adder 42, a negative-polarity oscillation signal Swsign from an output terminal d1 is inputted to another input terminal of the adder 42, and the oscillation signal Swsig is obtained at an output terminal of the adder 42 after being subtracted by an adder 42. Then, the oscillation signal Swsig inputted to the comparator 43 is binarized to generate a binary oscillation signal Wsig. An output terminal c2 and an output terminal d2 are grounded.

Here, the manner of operation of the above-mentioned feedback system is explained. An oscillation condition of the feedback system is that, to consider the feedback system as a loop transfer function, the feedback system has a gain of 0 db and a phase of 0°. Here, the resonance system of this embodiment formed of the movable member is considered as the second-order system and hence, the one-loop gain assumes a maximum value at the resonance frequency, and the phase is changed by 180° within an extremely small range in which the resonance frequency is used as a center frequency. Accordingly, by adjusting the delay or the advancement of the phase generated in each part preliminarily using a phase shift circuit 33 such that the phase assumes 0° at the resonance frequency, it is possible to accurately oscillate the feedback system at the frequency equal to the resonance frequency.

Here, when the adjustment of the phase in the phase shift circuit 33 is deviated, the oscillation frequency of the feedback system is slightly deviated from the resonance frequency and hence, the amplitude of the movable member is slightly decreased eventually. However, the phase is rapidly changed in the vicinity of the resonance frequency and hence, the deviation of oscillation frequency is trivial whereby the phase shift circuit 33 may perform the rough adjustment. Further, in this embodiment, with the provision of the AGC circuit 32, lowering of the amplitude can be corrected and hence, there arises no drawback.

The feedback system is formed of the positive feedback system and hence, the amplitude of the oscillation is increased along with time, and both the drive signal Hdsigp and the reverse phase drive signal Hdsign assume a square wave eventually whereby it is difficult to make the amplitude of the vibration of the movable member fall within a predetermined range. In this embodiment, with the provision of the AGC circuit 32, the amplitude of the vibration of the movable member is set to a predetermined value. That is, when the amplitude of the oscillation signal Swsig is smaller than the predetermined value, a gain in the AGC circuit 32 is increased, and when the amplitude of the oscillation signal Swsig is larger than the predetermined value, the gain in the AGC circuit 32 is decreased.

In this manner, the horizontal reflecting mirror 8 generates the twisting oscillation of the predetermined amplitude, the radiation direction of the light beam is changed, and the light spot on the retina 80*b* is stably scanned in the horizontal direction within a predetermined range.

Figure 9:
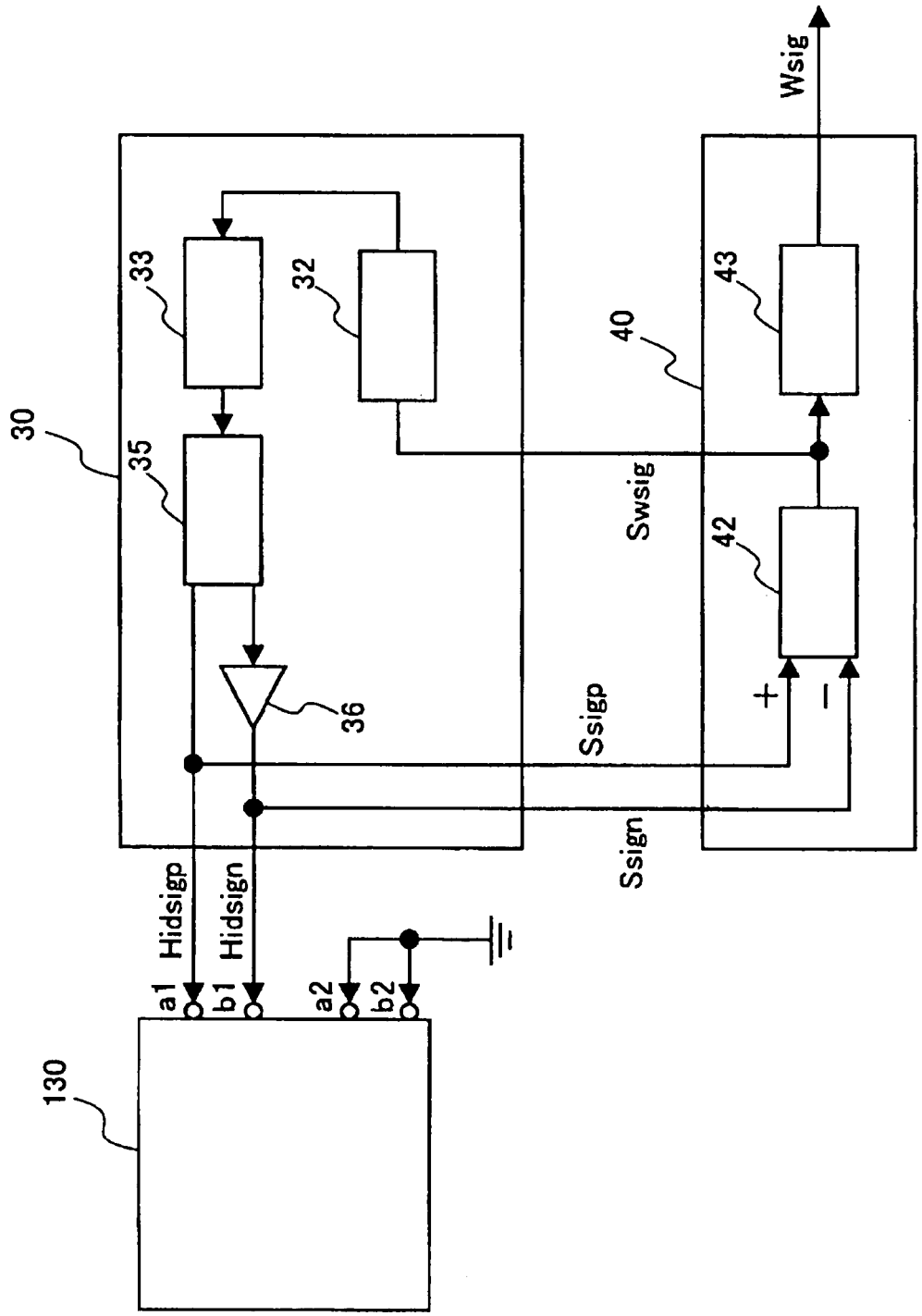
FIG. 9 is a block diagram of another horizontal scanning system.

Further, FIG. 9 shows another horizontal drive signal generator 37. In FIG. 9, a current amplifier 35 outputs a current Hdsigp of a magnitude corresponding to an input voltage, and an inverting current amplifier 36 outputs a current Hidsign with polarity obtained by inverting polarity of the current Hidsigp. Impedances of the driving piezoelectric element "a" and the driving piezoelectric element "b" are elevated at the resonance frequency and hence, voltages supplied to an input terminal a1 and an input terminal b1 are also increased corresponding to Q of the resonance system.

Accordingly, by feedbacking the voltage of the input terminal a1 or the input terminal b1, the feedback system can be oscillated. To summarize the above, according to this method, not to mention a detection piezoelectric element, without using any sensor, the oscillation signal Swsig is generated based on the current Hidisgp or the current Hidsign which is a horizontal drive signal, and the oscillation signal Swsig is fed back and hence, the movable member can be resonated at the resonance frequency.

Next, the vertical scanning part 63*b* is explained. The vertical scanning part 63*b* has a function of vertically scanning the light spot on the retina 80*b* by changing the radiation direction of the light beam. The vertical scanning part 63*b* includes a Galvano reflecting mirror 210 which constitutes an oscillation-type optical scanning mechanism for scanning the light spot in the vertical direction on the retina 80b, and a vertical drive signal generator 50 constituting a drive signal generator for supplying a drive signal to the Galvano reflecting mirror 210. The Galvano reflecting mirror 210 also forms a portion of the optical path portion.

The vertical scanning part 63b includes, as shown in FIG. 1, the Galvano reflecting mirror 210 as an oscillation reflecting mirror which performs mechanical deflection. The light beam radiated from the horizontal scanning part 63a is condensed by the second lens unit 62d and is incident on the Galvano reflecting mirror 210. The Galvano reflecting mirror 210 is, in response to a signal from the vertical drive signal generator 50 (see FIG. 10), oscillated about a rotational axis which intersects an optical axis of the laser beam incident on the Galvano reflecting mirror 210 such that the light spot on the retina 80b is scanned in the vertical direction.

Figure 10:
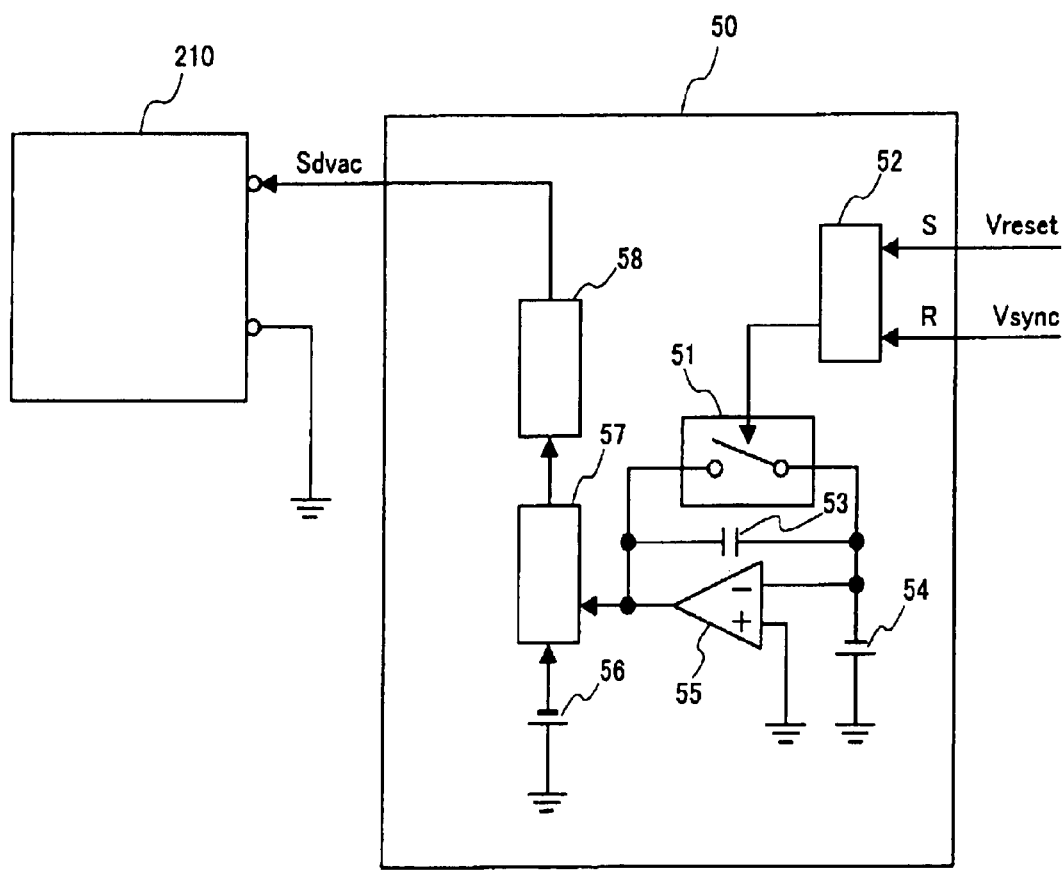
FIG. 10 is a block diagram of a drive signal generator of a vertical scanning system.
Figure 11:
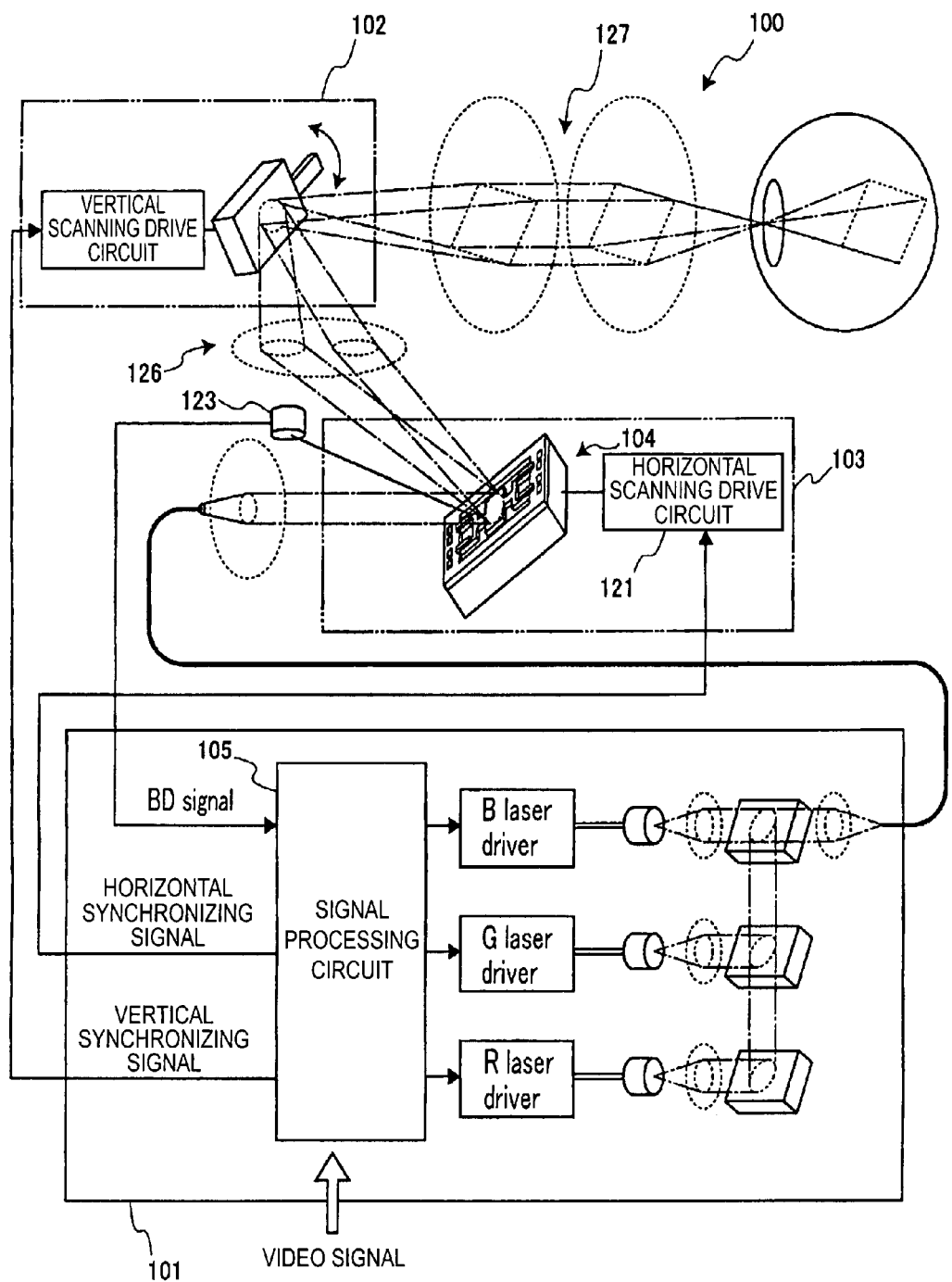
FIG. 11 is a view for showing a background art.

FIG. 10 shows the vertical drive signal generator 50. The vertical drive signal generator 50 includes, as constitutional elements thereof, an analog switch 51, an RS flip-flop 52, a capacitor 53, an integrated voltage source 54, an operational amplifier 55, an offset voltage source 56, an adder 57 and an amplifier 58.

The RS flip-flop 52 is set in response to a vertical synchronizing signal Vsync from the light beam generating part 11, and the RS flip-flop 52 is reset in response to a vertical scanning reset signal Vreset from the light beam generating part 11. When the RS flip-flop 52 is set, the analog switch 51 is turned off (terminated) and when the RS flip-flop 52 is reset, the analog switch 51 is turned on (conductive).

An integrator is constituted of the capacitor 53 and the operational amplifier 55. When the analog switch 51 is turned off, the integrator integrates a voltage of the integrated voltage source 54, and a voltage of an output terminal of the operational amplifier 55 is elevated with a fixed inclination with time. On the other hand, when the analog switch 51 is turned on, the voltage of the output terminal of the operational amplifier 55 assumes 0V. A negative voltage from the offset voltage source 56 is added to the voltage from the output terminal of the operational amplifier 55 by the adder 57. Due to such an addition of the voltage, the Galvano reflecting mirror 210 can be oscillated to a positive side and a negative side thus enlarging a scanning range of the light spot.

The amplifier 58 is provided for supplying electric power to the Galvano reflecting mirror 210. A vertical drive signal Sdvac shown in FIG. 5(C) is acquired at an output terminal of the amplifier 58, and is supplied to a drive coil (not shown in the drawing) of the Galvano reflecting mirror 210 and hence, the radiation direction of the light beam is changed corresponding to a voltage of the vertical drive signal Sdvac and the position of the light spot on the retina 80b is changed in the vertical direction.

The present invention provides the optical scanner which includes the light beam generating part which generates light beams in response to the image signal, the optical path part which guides the light beams to the projection screen, and the optical scanning part which changes the radiation direction of the light beams, wherein the optical scanning part includes the oscillation-type optical scanning mechanism which includes the movable member which resonates at the predetermined resonance frequency, the drive signal generator which generates the drive signal for allowing the movable member to resonate at the resonance frequency, and the oscillation signal generator which generates the oscillation signal in response to the change of the radiation direction of the light beams, and the light beam generating part includes the dot clock generator which generates the dot clock which becomes the reference of time-series processing by setting the frequency of the oscillation signal as the reference frequency.

Here, the optical scanner described in the embodiment merely constitutes one example of the present invention. That is, the present invention is not limited to the above-mentioned embodiment at all and it is easily conceivable that various modifications and various variations can be made without departing from the gist of the present invention.

For example, the light beam is not limited to the laser beam and may be a light beam generated by an LED light emitting element. The optical path part may be formed of any optical path member which is arranged in any optical path of the light beam provided that the optical path part can guide the light beam to the projection screen. In the optical scanning part, the scanning direction may be any direction provided that the optical scanning part can change the radiation direction of the light beam. The constitution of the oscillation-type optical scanning mechanism is not particularly limited provided that the oscillation-type optical scanning mechanism includes a movable member which resonates at a predetermined resonance frequency and a light beams are radiated to the movable member. Further, the drive signal generator may generate the drive signal based on any principle provided that the drive signal generator generates the drive signal which allows the movable member to resonate at the resonance frequency. Further, the oscillation signal generator may be any oscillation signal generator provided that the oscillation signal generator generates oscillating signals using or without using the sensor. Still further, the clock generated by the dot clock generator is not limited to the multiplied clock and may be any clock provided that the dot clock generator generates such a clock using the frequency of the oscillation signal as the reference frequency.

The present invention provides the control method of the optical scanner which scans a light spot on the projection screen by changing the radiation direction of light beams whose intensity is modulated based on the dot clock using the optical element, wherein the position of the light spot on the projection screen is oscillated at the resonance frequency intrinsic to the optical element, the oscillation signal is generated in response to the change of the radiation direction of the light beams, and the dot clock is generated using the frequency of the oscillation signal as the reference frequency.

Here, the optical scanner described in the embodiment merely constitutes one example of the present invention. That is, the present invention is not limited to the above-mentioned embodiment at all and it is easily conceivable that various modifications and various variations can be made without departing from the gist of the present invention.

For example, it is sufficient for the present invention that the radiation direction of the light beam is changed by the optical element and, eventually, the position of the light spot on the projection screen is changed, and the present invention is not limited by the manner of changing the radiation direction of the light beam. Further, the oscillation of the optical element at the intrinsic resonance frequency may be performed by any processing in the optical path, and the present invention is not limited by the direction along which the position of the light spot is oscillated. The present invention is also not limited with respect to the method for generating the oscillation signal and the method for multiplying the frequency of the oscillation signal. That is, the advantageous effects of the present invention are acquired by modulating the intensity of the light beam based on the dot clock.

Further, in this embodiment, the driving piezoelectric element "a" and the driving piezoelectric element "b" are fixedly mounted on the resilient member 12 and the resilient member 13 which belong to the first resilient member, and the detection piezoelectric element "c" and the detection piezoelectric element "d" are respectively fixedly mounted on the resilient member 15 and the resilient member 16 which belong to the second resilient member. However, the driving piezoelectric element "a" and the driving piezoelectric element "b" may be fixedly mounted on the resilient member 12 and the resilient member 15, and the detection piezoelectric element "c" and the detection piezoelectric element "d" are respectively fixedly mounted on the resilient member 13 and the resilient member 16. In this case, however, noises may be generated in the oscillation signal Swsig. In this respect, the former constitution is superior to the latter constitution.

Further, when the oscillation signal is not generated due to an impact from the outside or any abnormality or when the oscillation signal falls outside the predetermined range as the resonance frequency, the power source of the light beam generating part 11 may be turned off or the abnormality may be alarmed.

Further, when the control method of the optical scanner is configured such that a wavefront curvature modulating element is arranged between the first lens unit 62c and the horizontal scanning part 63a, and a wavefront curvature of the light beam is modulated based on a wavefront curvature modulating signal supplied from the light beam generating part 11, the wavefront curvature modulating signal may be generated based on the dot clock Dck.

According to the optical scanner and the controlling method thereof of the present invention, the movable member of the oscillation-type optical scanning mechanism is oscillated at a resonance frequency and hence, even when the resonance frequency of the movable member of the oscillation-type optical scanning mechanism is changed correspondingly to an environment such as temperature or moisture, it is possible to perform stable optical scanning irrespective of the difference in resonance frequency attributed to the individual difference of the oscillation-type optical scanning mechanism.

What is claimed is:

1. An optical scanner comprising:
    a light beam generating part which generates light beams in response to an image signal;
    an optical path part which guides the light beams to a projection screen; and
    an optical scanning part which changes the radiation direction of the light beams, wherein
    the optical scanning part includes:
    an oscillation-type optical scanning mechanism which includes a movable member which resonates at a predetermined resonance frequency for changing the radiation direction of the light beams;
    a drive signal generator which generates a drive signal for allowing the movable member to resonate at the resonance frequency; and
    an oscillation signal generator which generates an oscillation signal in response to a change of the radiation direction of the light beams, and
    the light beam generating part includes a dot clock generator which generates a dot clock which becomes the reference of time-series processing by setting a frequency of the oscillation signal as a reference frequency.

2. An optical scanner according to claim 1, wherein the oscillation-type optical scanning mechanism includes:
    a reflecting mirror which is fixed to the movable member and reflects the light beams;
    a first resilient member which is connected to the reflecting mirror and generates torsional oscillations; and
    a driving piezoelectric element which biases the first resilient member.

3. An optical scanner according to claim 2, wherein the oscillation signal generator includes:
    a second resilient member which is connected to the reflecting mirror and transmits the torsional oscillations; and
    a detecting piezoelectric element which generates the oscillation signal in response to a torsional quantity of the second resilient member.

4. An optical scanner according to claim 1, wherein the oscillation signal generator generates the oscillation signal from the drive signal.

5. An optical scanner according to claim 1, wherein the drive signal generator uses the oscillation signal as the drive signal by a positive feedback, and performs the oscillation.

6. An optical scanner according to claim 5, wherein the drive signal generator generates the drive signal which restricts the radiation direction of the light beam within a predetermined range.

7. An optical scanner according to claim 1, wherein the optical path part includes an optical element which corrects the passing direction of the light beams using an arc sine function.

8. An optical scanner according to claim 1, wherein the dot clock generator includes a phase-locked loop and generates a dot clock which becomes the reference of time-series processing by multiplying the frequency of the oscillation signal.

9. A control method of an optical scanner which scans a light spot on a projection screen by changing the radiation direction of light beams whose intensity is modulated based on a dot clock using an optical element, the method comprising:
    generating the light beams in response to an image signal;
    guiding the light beams to the projection screen;
    resonating a movable member at a predetermined resonance frequency for changing the radiation direction of the light beams;
    generating a drive signal for allowing the moveable member to resonate at the resonance frequency;
    generating an oscillation signal in response to a change of the radiation direction of the light beams; and
    generating the dot clock which becomes the reference of time series processing by setting a frequency of the oscillation signal as a reference frequency.

* * * * *